(12) United States Patent
Adachi et al.

(10) Patent No.: US 6,582,363 B2
(45) Date of Patent: Jun. 24, 2003

(54) VIDEO ENDOSCOPE SYSTEM AND ILLUMINATION OPTICAL SYSTEM

(75) Inventors: Rensuke Adachi, Tokyo (JP); Hideo Sugimoto, Tokyo (JP)

(73) Assignee: Pentax Corporation, Tokyo (JP)

( * ) Notice: Subject to any disclaimer, the term of this patent is extended or adjusted under 35 U.S.C. 154(b) by 49 days.

(21) Appl. No.: 09/934,605

(22) Filed: Aug. 23, 2001

(65) Prior Publication Data

US 2002/0026099 A1 Feb. 28, 2002

(30) Foreign Application Priority Data

Aug. 25, 2000 (JP) ........................................ 2000-254824
Oct. 30, 2000 (JP) ........................................ 2000-330303

(51) Int. Cl.$^7$ ............................. A61B 1/07; A61B 6/00
(52) U.S. Cl. ....................... 600/178; 600/160; 600/476; 600/478
(58) Field of Search ................................ 600/101, 160, 600/178, 181, 182, 476, 478; 362/574; 385/27, 31, 33

(56) References Cited

U.S. PATENT DOCUMENTS

| 4,464,705 A | * | 8/1984 | Horowitz | ...................... 362/12 |
| 5,143,435 A | * | 9/1992 | Kikuchi | ...................... 362/574 |
| 5,339,371 A | * | 8/1994 | Tomita | ...................... 385/24 |
| 5,881,196 A | * | 3/1999 | Phillips | ...................... 385/127 |
| 6,364,829 B1 | * | 4/2002 | Fulghum | ...................... 600/160 |

FOREIGN PATENT DOCUMENTS

WO  99/37204  7/1999

* cited by examiner

Primary Examiner—John P. Leubecker
(74) Attorney, Agent, or Firm—Greenblum & Bernstein, P.L.C.

(57) ABSTRACT

White light that was emitted from a white light source and converged through a condenser lens enters a light guide with a maximum incidence angle $\alpha$. Since excitation light emitted from an excitation light source is adjusted by the adjustment optical system for its beam diameter, it enters the light guide with a maximum incidence angle $\beta$ ($\beta<\alpha$) after being converged by the condenser lens. Then, a motion mechanism displaces a second lens in an adjustment optical system in the direction of the optical axis to vary the beam diameter and the maximum incidence angle $\beta$ of the excitation light, whereby a divergence angle of the excitation light emitted through a light distribution lens is made to correspond to the divergence angle of the visible light.

23 Claims, 20 Drawing Sheets

FIG.8A    FIG.8B
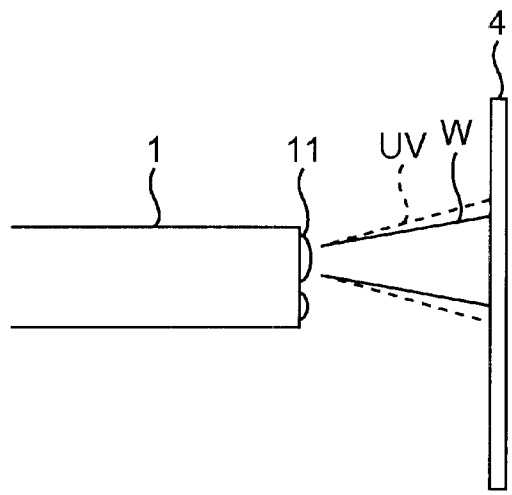
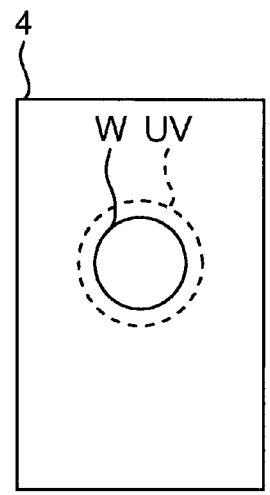
FIG.9
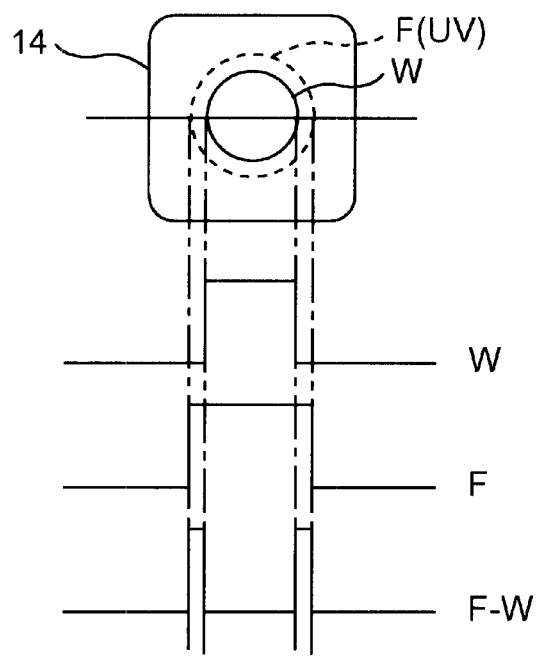

Tc

Ta  Ta

Tb

Tc

VIDEO ENDOSCOPE SYSTEM AND ILLUMINATION OPTICAL SYSTEM

BACKGROUND OF THE INVENTION

1. Field of the Invention

The present invention relates to a video endoscope system for fluorescence observations based on autofluorescence emitted from living tissue, and also relates to an illumination optical system used for such a video endoscope system. The present disclosure relates to object matter contained in Japanese Patent Applications No. 2000-254824 (filed Aug. 25, 2000) and 2000-330303 (filed Oct. 30, 2000) which is expressly incorporated herein by reference in its entirety.

2. Description of the Related Art

A conventional video endoscope system photographs images of fluorescence (autofluorescence) emitted from living tissue irradiated by excitation light such as ultraviolet light to enables an operator to observe fluorescence image of the living tissue. The intensity of autofluorescence emitted from diseased living tissue is lower than the intensity of autofluorescence emitted from healthy living tissue. Thus, the operator observing the fluorescence images of the object can recognize a region distinguished by lower autofluorescent intensity as an affected area with high potential for abnormalities.

Such a video endoscope system has a light source unit for alternately emitting visible light and excitation light, a light-guide optical system for guiding emitted visible light and excitation light as illuminating light, respectively, and a CCD for picking up the image of the object illuminated or irradiated by the illuminating light. While the visible light guided through the light-guide optical system illuminates the object, the CCD receives the visible light reflected by an object surface and outputs it as a reference image signal. When the excitation light guided through the light-guide optical system irradiates the object, the object emits autofluorescence, which is then picked up by the CCD and converted into a fluorescence image signal. Based on the reference image signal and the fluorescence image signal, a diagnostic image signal for the object is generated. For example, the fluorescence image signal is subtracted from any one of the three image signals corresponding to the three primary colors which constitutes the reference image signal to generate a diagnostic image signal. The diagnostic image signal causes a display device to display a diagnostic image on its screen. In the diagnostic image thus displayed, a portion of the object that does not emit autofluorescence is displayed as an image identical to that obtained by normal observation (monochromatic image or color image), whereas a portion of the object that emits autofluorescence is displayed as colored, such that the degree of coloring is proportional to autofluorescence intensity, which enable the operator to grasp the shape of the object by observing this diagnostic image and to recognize the intensity of the autofluorescence thereof.

FIG. 23 is a schematic diagram of the light guide optical system and the light source unit that constitute the conventional video endoscope system. As shown in this FIG. 23, the light guide optical system of this video endoscope system includes a light guide fiber bundle consisting of a number of optical fibers tied in a bundle (hereinafter abbreviated to as "light guide") 72 and a light distribution lens 73 for further spreading the illumination light emitted from this light guide 72. The light source unit has a condenser lens 71 for converging the illumination light emitted from a light source lamp (not shown in the figure) onto a proximal end face of the light guide 72. In such a configuration, the light source unit makes the visible light and the excitation light converted into collimated light beams incident on the condenser lens 71, respectively. The condenser lens 71 converges the visible light and the excitation light so that they enters the proximal end face of the light guide at maximum incidence angles α approximately identical to each other. The light guide 72 emits the visible light and the excitation light through its a distal end face, respectively. The emitted visible light and excitation light are diverged by a light distribution lens 73, respectively, to illuminate the object. Note that the angular aperture of the optical fiber becomes larger as the wavelength of light gets shorter, light guide 72 therefore emits excitation light with a larger angular aperture than that for the visible light. As a result, area δ irradiated by the excitation light through the light distribution lens 73 becomes wider than area γ illuminated by the visible light. As a result, in a portion of the diagnostic image that indicates the area δ irradiated with the excitation light but out of the area δ illuminated with the visible light, the condition of the object is not indicated rightly, which makes it difficult or impossible for the operator to correctly grasp the status of the object based on this diagnostic image.

SUMMARY OF THE INVENTION

It is the object of the present invention to provide a video endoscope system by which the area of the object illuminated with the visible light can be made to correspond to that irradiated with the excitation light and to provide an illumination optical system used for such a video endoscope system.

The illumination optical system according to the present invention includes as its components a light guide optical system that has a fiber bundle for emitting a light beam incident on its proximal end face through its distal end, a visible light lamp for generating visible light, a first optical system for collimating the visible light generated by the visible light lamp, an excitation light lamp for generating excitation light that excites living tissue to cause fluorescence, a second optical system for forming the excitation light generated by the excitation lamp into a beam whose diameter is smaller than that of the visible light collimated by the first optical system, a switching mechanism that alternately guides the visible light formed into the collimated light beam by the first optical system and the excitation light formed into the collimated light beam by the second optical system to a common optical path, and a condenser optical system for converging the visible light and the excitation light that are alternately guided by the switching mechanism onto the proximal end face of the fiber bundle.

By that structure, the diameter of the excitation light beam at the condenser optical system is less than that of the visible light. After the excitation light and the visible light being converged through the condenser lens, the maximum incidence angle of the excitation light with respect to the proximal end face of the fiber bundle becomes smaller than that of the visible light with respect to the proximal end face of the fiber bundle. As a result, the divergence angles of the visible light and of the excitation light emitted through the distal end face of the fiber bundle are made to correspond to each other.

BRIEF DESCRIPTION OF THE DRAWINGS

The invention will be described below in detail with reference to the accompanying drawings in which:

FIGS. 8A and 8B are explanatory illustrations of an irradiation area on the chart 4;

FIG. 9 is an explanatory illustration of an output signal from a digitizing circuit;

DESCRIPTION OF THE PREFERRED EMBODIMENT

Hereafter, preferred embodiments of a video endoscope system according to the present invention will be described with reference to the drawings.

First Embodiment

Figure 1:
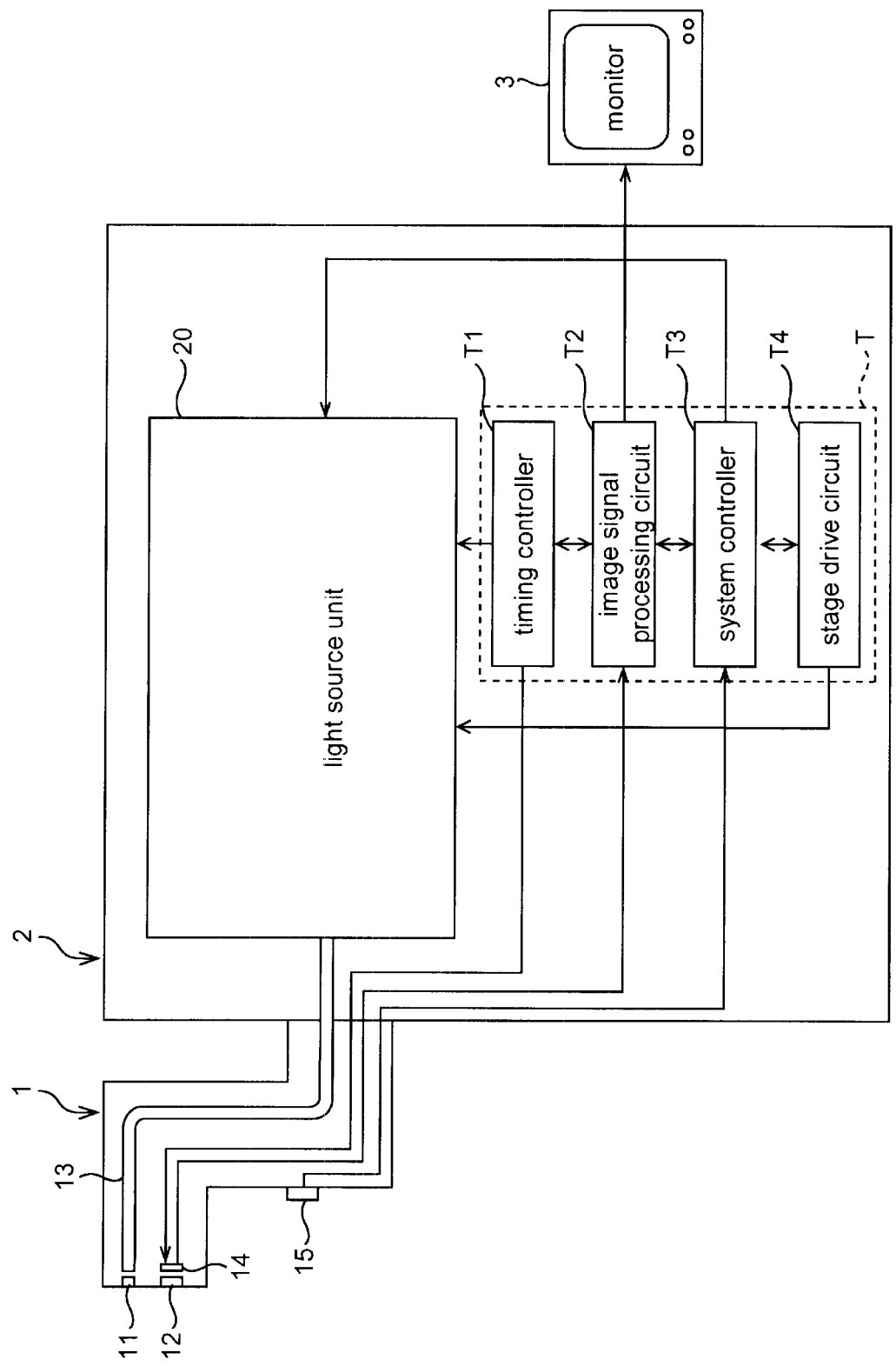
FIG. 1 is a block diagram showing a video endoscope system according to a first embodiment of the present invention.

FIG. 1 is a block diagram of the video endoscope system according to a first embodiment of present invention. As shown in FIG. 1, the video endoscope system has a video endoscope 1 and an external unit (a light source and a video processor) 2.

The video endoscope 1, whose concrete shape is not shown in FIG. 1, has an insertion part consisting of a flexible tube that is to be inserted into living body, an operating section that is integrally joined to a proximal end of the insertion part, and a light guide flexible tube that is integrally joined to the operating section and detachably connected to the external unit 2. A bending mechanism (not shown in the figure) is built into a predetermined area in the vicinity of the distal end of the insertion part, which is bent by manipulation of a dial installed on the operating section. A tip member (not shown in the figure) made of a hard material is fixed to a distal end of the insertion part. At least three through holes are formed in this tip member and, in two of these three through holes, a light distribution lens 11 and an objective lens 12 are respectively provided at the distal end thereof, and one of other through holes serves as a forceps channel. The operating section is provided with various kinds of operating switches besides the above-mentioned dial. Moreover, the video endoscope 1 has a light-guide fiber bundle composed of a number of optical fibers tied in a bundle (hereinafter, abbreviated to "light guide") 13. This light guide 13 was led through the insertion part, the operating section and the light-guide flexible tube, with its distal end face opposite the light distribution lens 11, and with its proximal end face inserted into the external unit 2. The light guide 13 and the light distribution lens 11 correspond to the light-guide optical system. Moreover, the video endoscope 1 has a CCD (charge-coupled device) area sensor 14 as an imaging device. An imaging plane of this CCD area sensor (hereinafter abbreviated to "CCD") 14 is arranged at a position where the objective lens 12 forms an image of an object of examination when the distal end of the insertion part faces the object. An excitation light cut-off filter (not shown in the figure) is disposed in the optical path between the objective lens 12 and the CCD 14. This excitation light cut-off filter blocks the excitation light (ultraviolet light) that excites living tissue to cause autofluorescence while transmitting visible light. The object lens 12 and the excitation light cut-off filter correspond to the objective optical system. Incidentally, numeral 15 in FIG. 1 schematically indicates one of a number of operating switches installed on the operating section of the video endoscope 1. This operation switch 15 is used to adjust the irradiation area described later.

Figure 2:
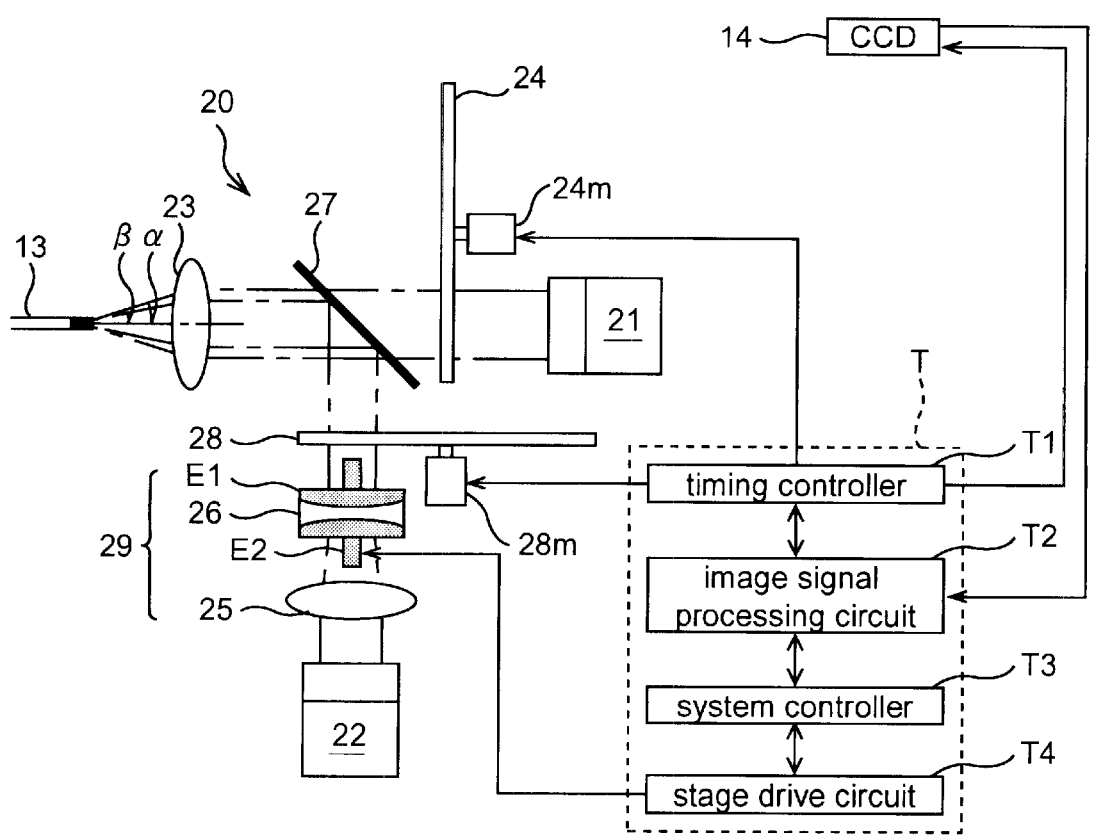
FIG. 2 is a block diagram showing an external unit including a light source and a processor.

As shown in FIG. 2, the external unit 2 is composed of a light source unit 20 and a processor T.

The light source unit 20 includes a white light source 21 and an excitation light source 22. The white light source 21 incorporates a xenon lamp and a reflector (not shown in the figure). The white light source 21 emits white light generated by the xenon lamp in the form of collimated light beam via reflection by the reflector. The white light source 21 corresponds to the visible light source. A condenser lens 23 positioned in the optical path of the white light emitted from the white light source 21 converges the white light incident thereon as collimated light beam onto its rear a focal point. Since the proximal end face of the light guide 13 is positioned at the rear focal point of this condenser lens 23, the maximum incidence angle α° of the white light with respect to light guide 13 becomes $\alpha° = \tan^{-1}(d_1/f)$, wherein the focal length f of the condenser lens 23 is denoted f, and the beam radius of the white light is denoted $d_1$.

Figure 3A:
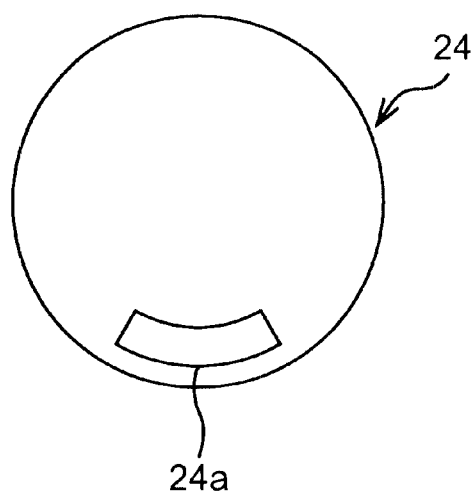
FIG. 3A is a front view of a rotary shutter 24.

A first rotary shutter 24 is positioned just behind the white light source 21 on the optical path of the white light emitted from the white light source 21. This first rotary shutter 24 corresponds to a first blocking member. As shown in FIG. 3A, the first rotary shutter 24 is a disc. One fan-shaped opening is bored along the circumference of the first rotary shutter 24. A transparent member of a parallel plate is fitted into this opening. This transparent member serves as a transmission part (visible light transmission part) 24a transmitting the white light. As shown in FIG. 2, this rotary shutter 24 is joined to the motor 24m so as to be rotated about its central axis set parallel to the optical path of the white light. While this rotary shutter 24 is rotated, the transmission part 24a is intermittently inserted into the optical path of the white light.

Figure 4A:
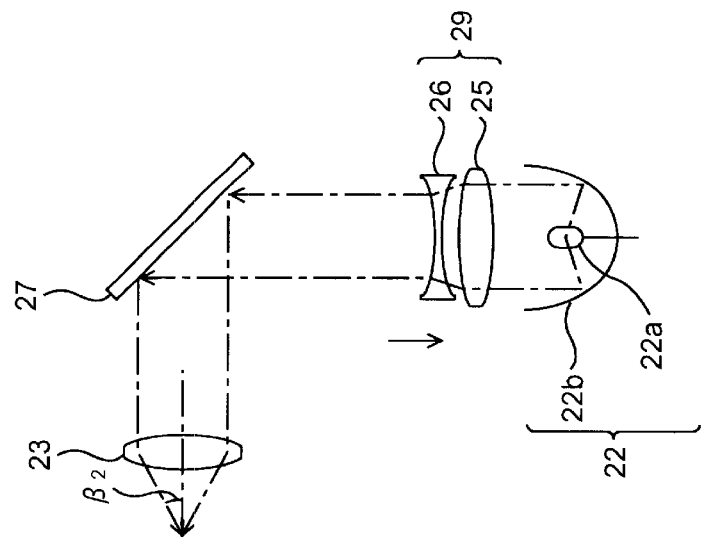
FIGS. 4A, 4B and 4C are explanatory illustrations of an adjustment optical system.
Figure 5:
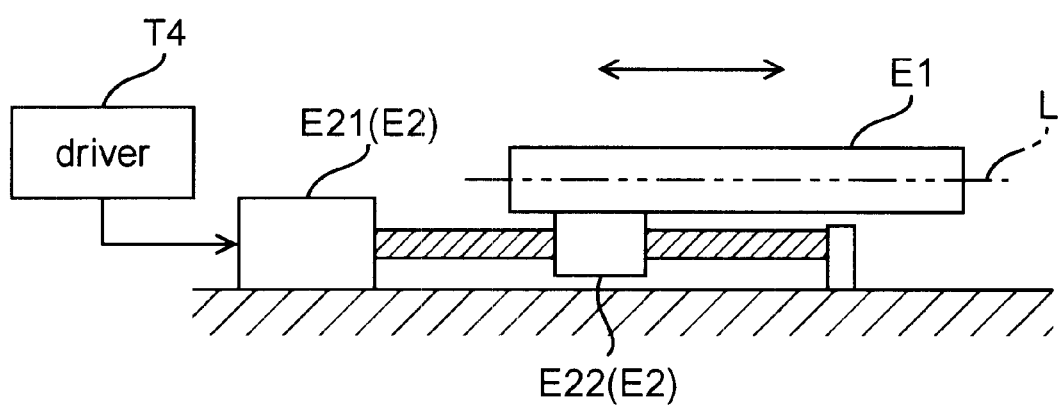
FIG. 5 is a side view of a move mechanism.

On the other hand, the excitation light source 22 includes a UV lamp 22a and a reflector 22b, as shown in FIG. 4A. The UV lamp 22a emits excitation light in the ultraviolet spectrum that excites living tissue to cause autofluorescence. The excitation light source 22 emits the excitation light generated by the UV lamp 22a as a collimated light beam via reflection by the reflector 22b. The beam diameter of the excitation light emitted from this excitation light source 22 coincides with the beam diameter of the white light emitted from white light source 21. An adjustment optical system 29 for adjusting the diameter of this excitation light beam is positioned on the optical path of the excitation light emitted from the excitation light source 22. This adjustment optical system 29 is composed of a first lens 25 that is a positive lens positioned just after the excitation light source 22, and a second lens 26 that is a negative lens positioned coaxially just after this first lens 25. This second lens 26 is held on a stage E1 that slides in the direction of the optical axis. This stage E1 is driven by a motion mechanism E2. Thus, the second lens 26 can be made to approach or recede from the first lens 25 by the motion mechanism E2. FIG. 5 is a side view of a concrete structure of the motion mechanism E2. The motion mechanism E2 has a linear guide L for guiding stage E1 only in the direction of the optical axis of the second lens 26, a motor E21, and a ball screw E22. A female screw portion of this ball screw E22 is fixed to a bottom surface of stage E1, and a male screw portion of this ball screw E22 is joined to a drive shaft of the motor E21. Incidentally, the ball screw E22 is disposed so that the central axis of its male screw is parallel to the sliding direction of the stage E1. The adjustment optical system 29, the stage E1 and the motion mechanism E2 correspond to a beam adjustment part. As shown in FIG. 4A, when the second lens 26 is placed at a standard position at which its front focal point coincides with the rear focal point of the first lens 25, the adjustment optical system 29 converts the collimated light beam emitted from the excitation light source 22 into a collimated light beam whose beam diameter is smaller than that of the emitted light beam. The optical path of the excitation light which has passed through the adjustment optical system 29 orthogonally crosses to the optical path of the white light, at a point between the rotary shutter 24 and the condenser lens 23. A half-mirror 27 is inclined to both the white light and the excitation light by 45 degrees at the point where these optical paths cross each other orthogonally. This half-mirror 27 transmits the white light, while reflecting the excitation light so as to travel along the same optical path as that of the white light. The excitation light reflected by this half-mirror 27 then enters the condenser lens 23 to be converged onto the proximal end face of the light guide 13. A beam radius $d_2$ of the excitation light entering the condenser lens 23 is reduced to be smaller than beam radius $d_1$ of the white light due to transmission through the adjustment optical system 29. Therefore, the maximum incidence angle $\beta°$ of the excitation light with respect to light guide 13 becomes $\beta° = \tan^{-1}(d_2/f)$ which is smaller than the maximum incidence angle $\alpha°$ of the white light.

Figure 3B:
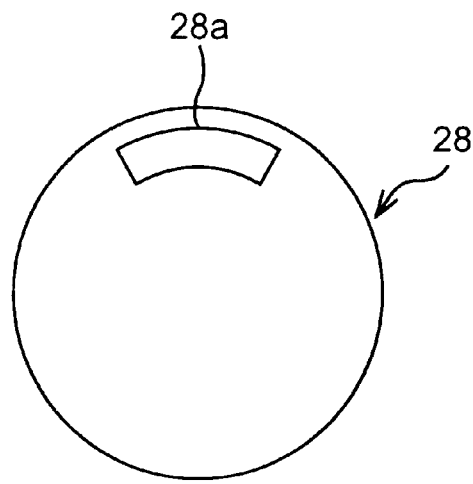
FIG. 3B is a front view of a rotary shutter 28.

A second rotary shutter 28 is disposed on the optical path of the excitation light between the adjustment optical system 29 and the half-mirror 27. This second rotary shutter 28 corresponds to the second blocking member. As shown in FIG. 3B, this second rotary shutter 28 is a disc, with one fan-shaped opening cut along its circumference. A transparent member of a parallel plate is fitted into this opening. This transparent member serves as a transmission part (excitation light transmission part) 28a transmitting the excitation light. As shown in FIG. 2, this rotary shutter 28 is joined to the motor 28m so as to be rotated about its central axis set parallel to the optical path of the excitation light. While this rotary shutter 28 is rotated, the transmission part 28a is intermittently inserted into the optical path of the excitation light.

Processor T is composed of a timing controller T1, an image signal processing circuit T2, a system controller T3, and a stage drive circuit T4, all of which are interconnected. As shown in FIG. 1, the system controller T3 is connected to the operating switch 15. When the operating switch 15 is actuated, the system controller T3 makes the stage drive circuit T4 execute adjustment of the irradiation area, which will be described later.

Figure 4B:
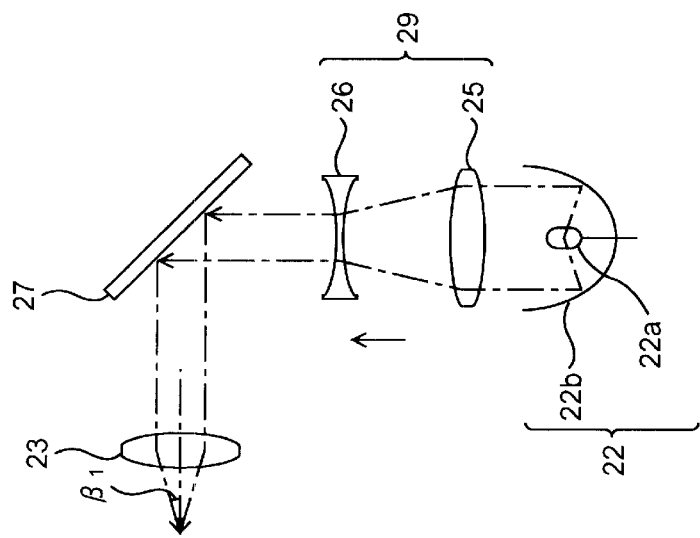
Figure 4C:
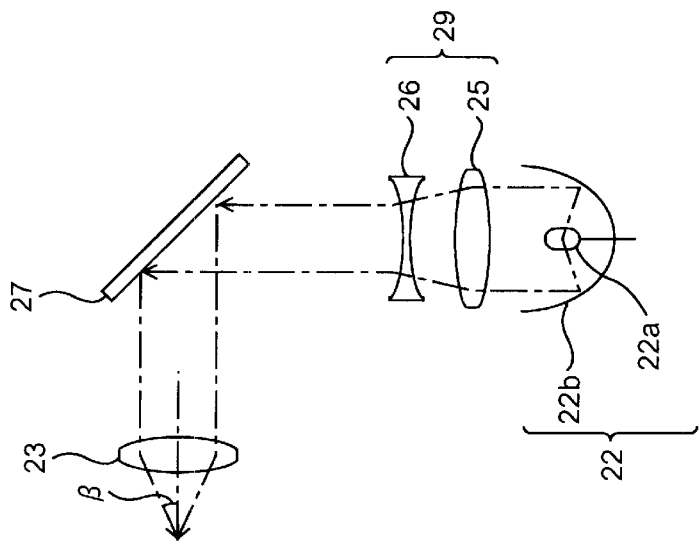

The stage drive circuit T4 controls the motor E21 of the motion mechanism E2 to move the stage E1, so that the second lens 26 moves back and forth along its optical axis. Here, when the stage E1 moves upward in FIG. 2, the second lens 26 recedes from the first lens 25, as shown in FIG. 4B, so that the beam diameter of the excitation light emitted from this second lens 26 becomes small. Thus, maximum incidence angle $\beta_1°$ of the excitation light converged by the condenser lens 23 with respect to the light guide 13 becomes narrower than that in the condition where the second lens 26 is placed at the standard position shown in FIG. 4A. On the other hand, when the stage E1 moves downward in the vertical direction shown in FIG. 2, the second lens 26 approaches the first lens 25, as shown in FIG. 4C, so that the beam diameter of the excitation light emitted from this second lens 26 becomes larger. Thus, the maximum incidence angle $\beta_2°$ of the excitation light converged by the condenser lens 23 with respect to the light guide 13 becomes larger than that in the condition where the second lens 26 is placed at the standard position shown in FIG. 4A. Thus, the stage drive circuit T4 can make the area irradiated with the excitation light and the area illuminated with the white light coincide with each other, by adjusting position of the second lens 26 through irradiation area adjustment which will be described later.

Figure 6:
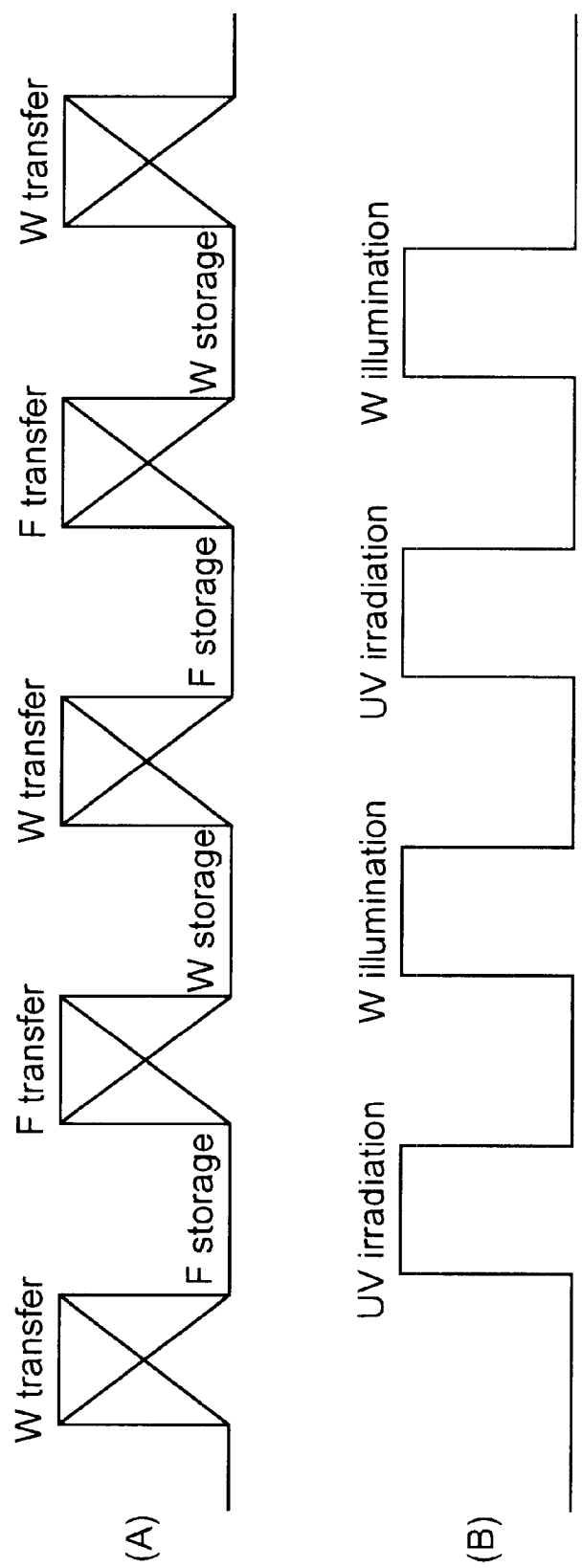
FIG. 6 is a timing chart of illumination and image acquisition.

The timing controller T1 is connected to the above-mentioned motors 24m, 28m, each of which corresponds to the switching drive mechanism, and rotates both motors 24m, 28m at constant speed in synchronism with each other. In the above-mentioned light source unit 20, the white light emitted from the white light source 21 toward the half-mirror 27 only while the transmission part 24a of the first rotary shutter 24 is inserted into the optical path. On the other hand, the excitation light emitted from the excitation light source 22 toward the half-mirror 27 only while the transmission part 28a of the second rotary shutter 28 is inserted into the optical path. The timing controller T1 rotates both motors 24m, 28m at a constant speed in synchronism with each other so that the transmission part 28a is inserted into the optical path during the period in which the transmission part 24a is not inserted into the optical path, and so that the transmission part 24a is inserted into the optical path during the period in which the transmission part 28a is not inserted into the optical path. As a result, the white light and the excitation light are incident on the half-mirror 27 alternately and repeatedly. The white light having passed through the half-mirror 27 is converged onto the proximal end face of the light guide 13 by the condenser lens 23. On the other hand, the excitation light reflected by the half-mirror 27 is converged onto the vicinity of the proximal end face of the light guide 13 by the condenser lens 23. Then, the white light and the excitation light are alternately guided by the light guide 13, traveling to the light distribution lens 11. Accordingly, the white light and the excitation light are emitted through the light distribution lens 11 alternately and repeatedly. While the object is illuminated by the white light, the light reflected from the surface of the object is focused by the objective lens 12 to form an object image on the imaging plane of the CCD 14. This object image is converted into an image signal by the CCD 14. On the other hand, while this object is irradiated by the excitation light, this object emits autofluorescence. Therefore, the autofluorescence emitted from the object as well as the excitation light reflected by the object surface enters the objective lens 12. However, since the excitation light is blocked by the excitation light cut-off filter not shown in the figure, the image of the object only from the autofluorescence is formed on the imaging plane of the CCD 14. The CCD 14 is connected to the timing controller T1 and the image signal processing circuit T2, respectively, and outputs the image signal, which is to enter the image signal processing circuit T2, according to the drive signal transmitted from the timing controller T1. FIG. 6 is a timing chart for the illumination for the tissue and the image acquisition, wherein a symbol (A) represents a driving signal for the CCD 14 output from the timing controller T1 and wherein a symbol (B) represents an irradiation period within which the excitation light (UV) or the white light (W), is emitted through the light distribution lens 11 to irradiate the object. As shown in FIG. 5, the period of "UV irradiation" during which the excitation light is emitted through the light distribution lens 11 corresponds to the period of "F accumulation" for the CCD 14. Therefore, in a state in which the object is irradiated with the excitation light, electric charges corresponding to the object image formed from autofluorescence are accumulated in each pixel of the CCD 14. The electric charges thus accumulated are transmitted during the following "F transmission" period to the image signal processing circuit T2 as an F image signal (fluorescence image signal). On the other hand, a period of "W illumination" during which the white light is emitted through the light distribution lens 11 corresponds to a period of "W accumulation" for the CCD 14. In the state in which the object is illuminated with the white light, electric charges are accumulated in each pixel of the CCD 14 corresponding to the object image formed from the white light. The electric charges thus accumulated are transmitted to the image signal processing circuit T2 as a W image signal (reference image signal) during the next "W transfer" period.

Figure 7:
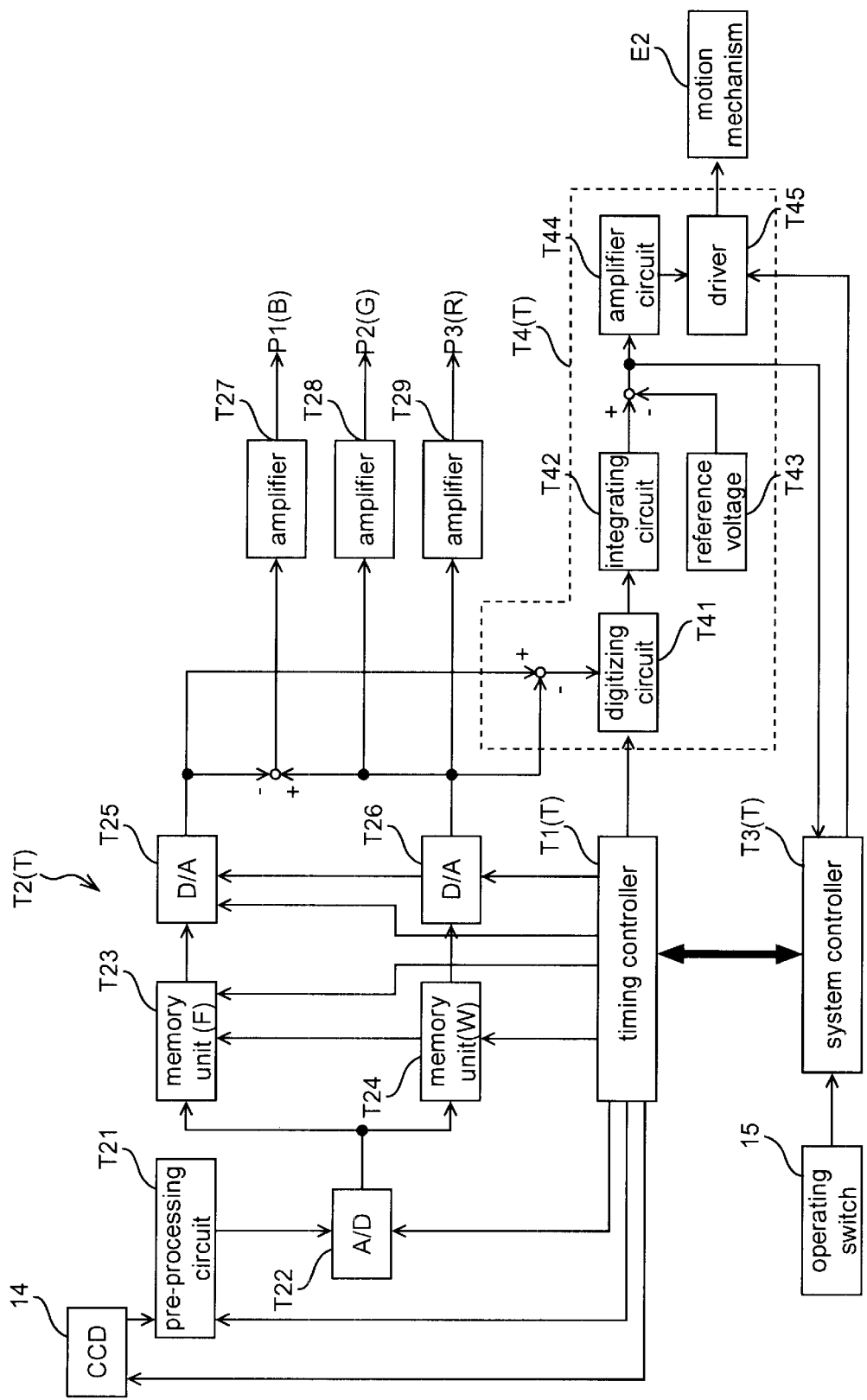
FIG. 7 is a block diagram showing the configuration of the processor.

Image signal-processing circuit T2 generates a diagnostic image signal indicating the object based on the F image and the W image signals, then displays the diagnostic image on a monitor 3, based on the diagnostic image signal generated. Hereafter, with reference to FIG. 7 which is a detailed block diagram showing the image signal processing circuit T2 and the stage drive circuit T4, concrete contents of processing executed in this image signal processing circuit T2 will be described. As shown in FIG. 7, the image signal processing circuit T2 has a pre-processing circuit T21, an A/D converter T22, a pair of memory units T23, T24, a pair of D/A converters T25, T26 which are connected to the timing controller T1, and first to third amplifiers T27–T29. The pre-processing circuit T21 is connected to the CCD 14 which outputs the F image signal and the W image signal alternately and repeatedly. This pre-processing circuit T21 receives image signal output from the CCD 14, performs amplification and $\gamma$ correction thereon, and outputs it. More specifically, the pre-processing circuit T21 amplifies the F image signal and the W image signal while switching the amplification factor for the F image signal and the amplification factor for the W image signal dynamically, based on the signals from timing controller T1, so that the levels of the peak values of the W image signal and the F image signal may become the same. The A/D converter T22 analog-to-digital converts the image signal output from the pre-processing circuit T21 into digital image data to output it. Therefore, the F image signal and the W image signal are then converted into F image data and W image data through signal processing performed by the pre-processing circuit T21 and the A/D converter T22, respectively. As a result, the F image data and W image data are output from the A/D converter T22 alternately. Each of the memory units T23, T24 has a storage area capable of storing data for all pixels of CCD 14. Each data of a pixel consists of predetermined multiple bits. Each of the memory units T23, T24 is connected to the A/D converter T22, respectively. Further, in each of the memory units T23, T24 is stored image data output from the A/D converter T22 for a period specified by timing controller T1. More specifically, while the A/D converter T22 outputs the F image data, this F image data is stored in the first memory unit T23, and while the A/D converter T22 outputs the W image data, this W data is stored in the second memory unit T24. The D/A converters T25, T26 are connected to the memory units T23, T24, respectively. The first D/A converter T25 converts the F image data output from the first memory unit T23 into an analog F image signal to output it. The second D/A converter T26 converts the W image data output from the second memory unit T24 into an analog w image signal to output it.

A difference between the W image signal output from the second D/A converter T26 and the F image signal output from the first D/A converter T25 is input to the first amplifier T27. More specifically, a signal obtained by subtracting the F image signal from the W image signal is input to the first amplifier T27. On the other hand, the W image signal output from the second D/A converter T26 is input to the second amplifier T28 and to the third amplifier T29. A set of signals to be input to the amplifiers T27–T29 correspond to the diagnostic image signal. Therefore, this diagnostic image signal includes a signal obtained by a subtraction circuit provided between the output terminals of both D/A converters T25, T26 and the first amplifier T27, and W image signal output from the second D/A converter T26. The amplifiers T27–T29 then amplify the respective input signals at predetermined amplification factors to output them to output terminals P1–P3, which are to be connected to a monitor. More specifically, the monitor 3 has an input terminal for the B signal component, an input terminal for the G signal component, and an input terminal for the R signal component. The first output terminal P1 is connected to the input terminal for the B signal component of the monitor 3, the second output terminal P2 is connected to an input terminal for the G signal component of the monitor 3, and the third output terminal P3 is connected to the input terminal for the R signal component of the monitor 3. Further, the image signal processing circuit T2 has an output terminal (not shown in the figure) for output of a synchronization signal to permit display of moving images, according to a predetermined format. On the other hand, the monitor 3 has an input terminal (not shown in the figure) for this synchronization signal. The output terminal for the synchronization signal of the image signal processing circuit T2 and the input terminal for the synchronization signal of the monitor 3 are connected. The monitor 3 displays the diagnostic image of the object as a moving picture on its screen based on the signals input to its input terminals, respectively. If only the W image data is output through the output terminals P1–P3, a monochromatic image of the object illuminated with white light would be displayed on the monitor 3. However, as it is, the image signal formed by subtracting the F image signal from the W image signal is output through the first output terminal P1 as described above. Therefore, in the diagnostic image displayed on the monitor 3, an area corresponding to a portion of the object that does not emit autofluorescence is indicated as a monochromatic image of the same portion, whereas an area corresponding to a portion of the object that emits autofluorescence is indicated as a specific color image according to the intensity of the autofluorescence. This allows the operator to correctly recognize the shape of the object and to grasp the intensity distribution of the autofluorescence by observing the diagnostic image displayed on this monitor 3. In other words, the operator can distinguish a region of the object that generates strong autofluorescence, and hence is healthy, from a portion that generates weak autofluorescence, and hence is diseased.

However, if the area of the object irradiated with the excitation light and the area illuminated with the white light do not coincide with each other, a portion of the diagnostic image which is within the area irradiated with the excitation light but out of the area illuminated with the white light do not correctly indicate the condition of the object. For this reason, it is necessary to perform the irradiation area adjustment before actual observation for an object, so that the area irradiated with the excitation light may be coincide with the area illuminated with the white light. This irradiation area adjustment is performed with the distal end of the video endoscope 1 opposed to a chart 4, as shown in FIG. 8A, before the observation for the object. This chart 4 is a tabular member having a planar geometry shown in FIG. 8B. Fluorescent paint is applied to a surface of the chart 4 so that the intensity of the white light reflected by the chart 4 at the time when it is illuminated with the white light of a predetermined intensity may be equal to the intensity of the reflected white light at the time when the object is illuminated with the white light, and so that the intensity of the fluorescence emitted from the chart 4 at the time when it is irradiated with the excitation light of a predetermined intensity may be equal to the intensity of the autofluorescence at the time when the object is illuminated. The operator starts the adjustment by actuating the operating switch 15 with the distal end of the video endoscope 1 facing the chart 4. Then, the system controller T3 commands the stage drive circuit T4 to adjust the irradiated area according to this instruction.

The stage drive circuit T4, as shown in FIG. 7, has a digitizing circuit T41, an integrating circuit T42, a reference voltage block T43, an amplifier circuit T44 and a driver T45. For each pixel, the stage drive circuit T4 subtracts the W image signal output from the second D/A converter T26 from the F image signal output from the first D/A converter T25 with a subtraction circuit provided between the output terminals of both D/A converters T25, T26, and the digitizing circuit T41, sending difference value obtained through the subtraction to the digitizing circuit T41. The digitizing circuit T41 is also connected to the timing controller T1, so that it holds only the difference value between the F image signal and the W that correspond to one predetermined line in the CCD 14 and digitizes the held difference value with reference to a predetermined threshold. FIG. 9 illustrates the difference signal output from this digitizing circuit T41. As shown in FIG. 9, on the imaging plane of CCD 14, the image of the object generated from autofluorescence at the time when the object is irradiated with the excitation light and the image of the object at the time when the same object is illuminated with the white light are formed alternately. Here, when the area of the object irradiated with the excitation light is broader than the area illuminated with the white light, the differential signal (F-W) between the F image signal and the W image signal that corresponds to an area, which is irradiated or illuminated with one of the excitation light and the illumination light, does not become zero. When both the illuminated area and the irradiated area coincide, the differential signal between the F image signal and the W image signal keeps being zero. The integrating circuit T42 shown in FIG. 7 integrates the differential signal (F-W) between the F image signal and the W image signal over one line in the CCD 14. Whenever a value of the differential signal between the F image signal and the W image signal is zero over one line, a value of the integral signal output from this integrating circuit T42 also becomes zero. However, the integrating circuit T42 may actually has an output characteristics that it outputs a non-zero value (which is called offset value) in such cases. To deal with such characteristics, the offset value is compensated by subtracting a predetermined reference voltage supplied by the reference voltage block T43 from the integral signal output form this integrating circuit T42. As a result, whenever the value of the differential signal between the F image signal and the W image signal is zero over one line, the value of the difference (which is called error signal) between the integral signal output from the integrating circuit T42 and the output signal of the reference voltage block T43 becomes zero. Note that, whenever the area of the object irradiated with the excitation light is broader than the area illuminated with the white light, the value of this error signal becomes positive. On the other hand, whenever the area of the object irradiated with the excitation light is smaller than the area illuminated with the white light, the value of this error signal becomes negative. This error signal is amplified by the amplifier circuit T44 and then input to the driver T45. This driver T45 together with motor E21 of the motion mechanism E2 are connected to the system controller T3. When the operating switch 15 is actuated, the system controller T3 operates the driver T45, so that the driver T45 rotates motor E21 forward or in reverse, based on the error signal amplified by the amplifier circuit T44. Concretely, if the error signal is positive, the driver T45 rotates the motor E21 in a positive direction. Then, the male screw of the ball screw E22 rotates in the positive direction, so that the stage E1 displaces the second lens 26 away from the first lens 25 (upward, in FIG. 2). On the other hand, when the error signal is negative, the driver T45 rotates the motor E21 in the reverse direction. Then, the male screw of the ball screw E22 rotates in the reverse direction, so that the stage E1 displaces the second lens 26 closer to the first lens 25 (downward, in FIG. 2). The system controller T3 monitors the error signal and enables the driver T45 from the time at which the operating switch is actuated until the value of the error signal becomes zero. When the error signal reaches zero, the system controller T3 stops the operation of the driver T45, and the stage E1 is fixed at a position where the error signal becomes zero.

Figure 10:
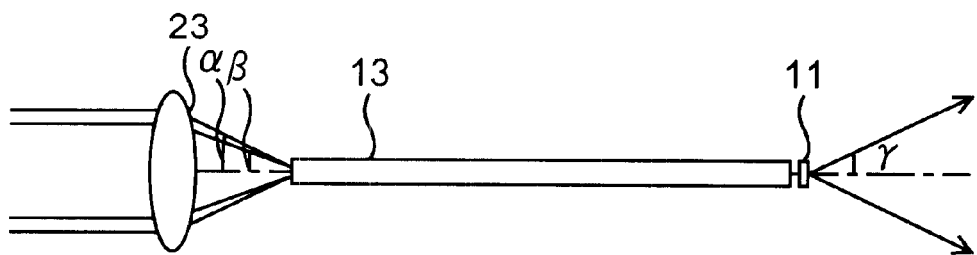
FIG. 10 is an explanatory illustration showing the irradiation areas by white light and by excitation light after adjustment of the irradiation area.

FIG. 10 is an explanatory illustration showing the irradiated area when the error signal becomes zero. As shown in FIG. 10, the maximum incidence angle $\beta$ of the excitation light with respect to the light guide 13 at this moment is smaller than the maximum incidence angle α of the white light. Note that the light guide 13 emits the white light, which has been incident on its proximal end face at the maximum incidence angle α, through its distal end face with a predetermined first divergence angle. The emitted white light is further diverged through the light distribution lens 11, with the maximum divergence angle γ. On the other hand, the excitation light enters the proximal end face of the light guide 13 at the maximum incidence angle β smaller than α and subsequently is emitted through the distal end face with a predetermined second divergence angle smaller than the above-mentioned first divergence angle. The emitted excitation light is further diverged through the light distribution lens 11. This light distribution lens 11 possesses chromatic aberration of magnification, so that the light distribution lens 11 would diverge the excitation light at a larger exit angle than that of the white light which has entered the light distribution lens 11 at the same incidence angle as the white light. On the other hand, in this embodiment, since the excitation light is emitted from the light guide 13 at a smaller divergence angle than that of the white light, the light distribution lens 11 emits this excitation light with the same divergence angle γ as that of the white light. As a result, the area of the object irradiated with the excitation light coincides with the area illuminated with the white light.

As described above, the operator can easily makes coincidence between the area illuminated with the white light and the area irradiated with the excitation light, by pushing an operating button 15 with the distal end of the video endoscope 1 opposed to the chart 4. Then, the operator can obtain the diagnostic image that correctly indicates the state of an object, by photographing the object in a state that both areas coincide with each other. Therefore, accuracy of the diagnosis conducted based on this diagnostic image is improved.

Second Embodiment

Figure 11:
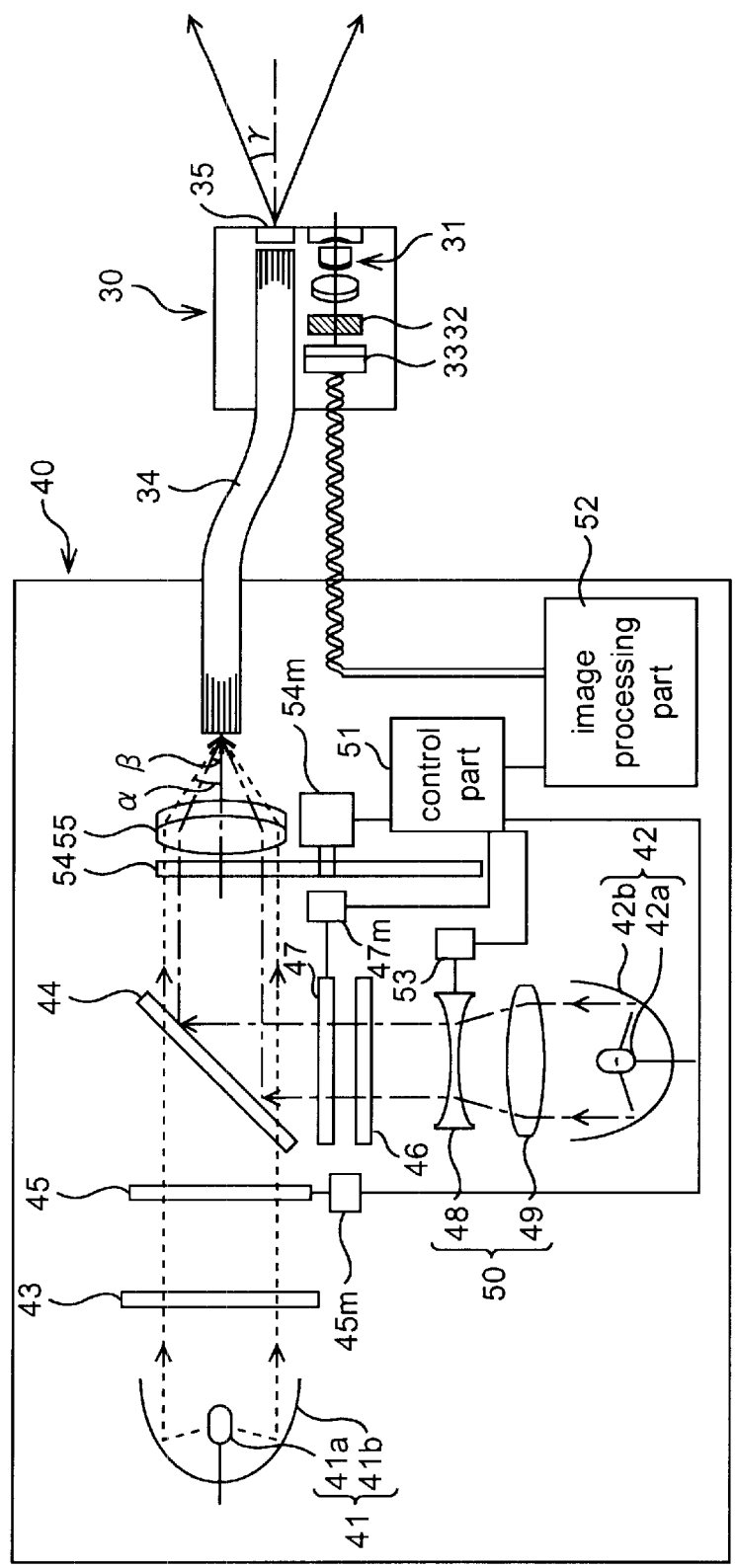
FIG. 11 is a block diagram showing a video endoscope system according to the second embodiment of the present invention.

The second embodiment of present invention is characterized in that, as compared with the above-mentioned first embodiment, the reference image signal is not a monochromatic signal but a color signal. FIG. 11 is an outline block diagram of the video endoscope system according to the second embodiment. As shown in FIG. 11, the video endoscope system has a video endoscope 30 and an external unit 40.

Although FIG. 11 does not show a concrete shape of the video endoscope 30, the video endoscope 30 has an insertion part of a flexible tube, an operating section that is integrally joined to the proximal end of the insertion part, and a light guide flexible tube that is integrally joined to the operating section and detachably connected to the external unit 40. A bending mechanism (not shown in the figure) is built into a predetermined area in the vicinity of the distal end of the insertion part, which is bent by manipulation of a dial provided on the operating section. A tip member (not shown in the figure) made of a hard material is fixed to a distal end of the insertion part. At least three through holes are formed in this tip member. In two of these three through holes, a cover glass 35 which is a transparent member of a parallel plate and an objective lens (objective optical system) 31 are respectively provided at a distal end part thereof, and one of other through holes serves as a forceps channel. In addition to the above-mentioned dial, various types of operating switches are provided on the operating section. Further, the video endoscope 30 has a light-guide fiber bundle (hereinafter abbreviated to "light guide") 34 composed of a number of optical fibers tied in a bundle. This light guide 34 was led through the insertion part, the operating section and the light-guide flexible tube with its distal end face opposite the cover glass 35 and with its proximal end face is inserted into the external unit 40. Moreover, the video endoscope 30 has an excitation light cut-off filter 32 and a CCD (charge-coupled device) 33 as an imaging device. An imaging plane of this CCD 33 is arranged at a position at which objective lens 31 forms an image of an object of examination when the distal end of the insertion part faces the object. The excitation light cut-off filter 32 is disposed in the optical path between the objective lens 31 and the CCD 33, to block the excitation light (ultraviolet light) that excites the living tissue to cause autofluorescence, while transmitting visible light.

The external unit 40 includes a white light source 41 and an excitation light source 42. The white light source 41 incorporates a xenon lamp 41a for emitting white light and a reflector 41b. An internal surface (reflective surface) of the reflector 41b is formed as a paraboloid of revolution. The xenon lamp 41a is disposed at a focal position of the paraboloid of revolution of this reflector 41b. The light emitted from the xenon lamp 41a is collimated through the reflection by the reflector 41b. On the other hand, the excitation light source 42 has a UV lamp 42a for emitting light, including ultraviolet light, and a reflector 42b. An internal surface (reflective surface) of this reflector 42b is formed as a paraboloid of revolution. Note that the UV lamp 42a is arranged at a focal position of the paraboloid of revolution of this reflector 42b. Further, the light emitted from this UV lamp 42a is collimated through reflection by the reflector 42b. Note that since both reflectors 41b, 42b are the same size, the beam diameter of the white light emitted from the white light source 41 is identical to the beam diameter of the excitation light emitted from the excitation light source 42.

In the optical path of the collimated light beam emitted from the white light source 41 are arranged an infrared cut-off filter 43, a first shutter 45, and a dichroic mirror 44, in order. The infrared cut-off filter 43 blocks wavelength components in the infrared spectrum of the white light emitted from the white light source 41, while transmitting wavelength components in the visible spectrum. The first shutter 45 is joined to a first shutter drive mechanism 45m, which drives the first shutter 45, so that the white light passing through the infrared cut-off filter 43 is intermittently blocked or allowed to pass therethrough. The dichroic mirror 44 transmits wavelength components in the visible spectrum of the light incedent thereon while reflecting wavelength components in the ultraviolet spectrum. Thus, the white light in the visible spectrum that has passed through the first shutter 45 passes through this dichroic mirror 44.

The excitation light source 42 is arranged so that the light emitted therefrom orthogonally crosses the optical path of the white light passing through the dichroic mirror 44 on the reflective surface of the dichroic mirror 44. In the optical path between this excitation light source 42 and the dichroic mirror 44 are arranged an adjustment optical system 50, an excitation light filter 46, and a second shutter 47, in that order. The adjustment optical system 50 for adjustment of the beam diameter of the excitation light is composed of a first lens 49 which is positioned just after the excitation light source 42 and which is a positive lens serving as a convergent optical system and a second lens 48 which is positioned just after the first lens 49 coaxially and which is a negative lens serving as a divergent optical system. This second lens 48 is held by a sliding mechanism 53 in a manner that it can slide in the direction of the optical axis. The standard position of this second lens 48 is such that its front focus coincides with a rear focus of the first lens 49 and it constitutes an afocal optical system together with the first lens 49. The collimated light beam emitted from the excitation light source 42 is converged by the first lens 49. The convergent beam emitted from this first lens 49 enters the second lens 48 and is converted into a collimated light beam through this second lens 48. Therefore, the diameter of the collimated light beam emitted from the second lens 48 becomes smaller than the diameter of the collimated light beam emitted from the excitation light source 42. The excitation light filter 46 transmits only wavelength components in the region used for the excitation light in the light emitted from the excitation light source 42. Here, this excitation light is ultraviolet light that excites living tissue to cause autofluorescence. The second shutter 47 is joined to a second shutter drive mechanism 47m. The second shutter drive mechanism 47m drives the second shutter 47, so that the excitation light that has passed through the excitation light filter 46 is intermittently blocked or allowed to pass therethrough. The excitation light that has passed through this second shutter 47 is reflected by the dichroic mirror 44. An optical path of the excitation light reflected by this dichroic mirror 44 lies on an axis common to the optical path of the white light passing through the dichroic mirror 44. Note that the shutters 45, 47, the shutter drive mechanisms 45m, 47m, and the dichroic mirror 44 correspond to the switching mechanism.

In the optical path in the rear of the dichroic mirror 44 are arranged a wheel 54 and a condenser lens 55, in that order. The wheel 54 is a disc, with four openings formed along its circumference. These openings are fitted with a blue filter transmitting only blue light (B), a green filter transmitting only green light (G), a red filter transmitting only red light (R) and a transparent member transmitting the excitation light. This wheel 54 is joined to a motor 54m, which rotates the wheel 54 so that the blue filter, the green filter, the red filter, and the transparent member are repeatedly and sequentially inserted into the optical path. Incidentally, during a period when any one of the filters of the wheel 54 is inserted into the optical path, the first shutter 45 allows the white light to pass therethrough while the second shutter 47 blocks the excitation light. Therefore, only the white light enters the dichroic mirror 44. This white light is converted into blue light, green light, and red light through the blue filter, the green filter, and the red filter of wheel 54, respectively, in sequence and then travels to the condenser lens 55. On the other hand, during the time in which the transparent member of the wheel 54 is inserted into the optical path, the first shutter 45 blocks the white light while the second shutter 47 transmits the excitation light. Therefore, only the excitation light enters the dichroic mirror 44 to be reflected. This excitation light then passes through the transparent member of the wheel 54 and then travels to the condenser lens 55. The condenser lens 55 converges the light onto a proximal end face of the light guide 34. Thus, the blue light, green light, red light, and the excitation light enter this light guide 34 repeatedly, in the same sequence. The entered light is guided through the light guide 34 and emitted from the distal end of the video endoscope to the object. Accordingly, this object is irradiated by the blue light, the green light, the red light, and the excitation light repeatedly, in the same sequence. Note that the visible light (blue light, green light, and red light) that has passed through the dichroic mirror 44 is converged through this condenser lens 55 in such away that the maximum incidence angle $\alpha°$ of the visible light with respect to the light guide 34 becomes equal to or less than the angular apperture of the light guide 34 for the red light, and then enters the light guide 34. On the other hand, since the beam diameter of the excitation light reflected by the dichroic mirror 44 is smaller than the beam diameter of the visible light, the excitation light is converged in such a way that the maximum incidence angle $\beta°$ thereof becomes smaller than angle $\alpha°$, and then enters the light guide 34. The red light guided through the light guide 34 is emitted from its distal end face as a divergent beam with the divergence angle $\gamma°$. On the other hand, the excitation light guided through the light guide 34 is emitted from its distal end face as a divergent beam with divergence angle $\gamma°$.

It should be noted that if the area of the object irradiated with the visible light (red light) and the area illuminated with the excitation light do not coincide due to geometrical errors, its manufacturer or the operator is expected to adjust the position of the second lens 48 in the direction of the optical axis by controlling the sliding mechanism 53 through a control part 51, as in the case of the above-mentioned first embodiment. Through this adjustment, the maximum incident angle $\beta°$ of the excitation light with respect to the light guide 34 increases in case the second lens 48 is displaced closer to the first lens 49 or decreases in case the second lens 48 is displaced away from the first lens 49, the divergence angle of the excitation light emitted from the light guide 34 is made to agree with the divergence angle of the visible light (red light). Moreover, when the above-mentioned video endoscope 30 is detached from the external unit 40 and replaced with other video endoscopes, the manufacturer or the operator can make the divergence angle of the excitation light emitted from light guide 34 agree with the divergence angle of the visible light (red light) by adjusting the position of the second lens 48 in accordance with characteristics of the new video endoscope.

Whenever the light guide 34 emits blue light, green light, or red light upon the object, the objective lens 31 of the video endoscope 30 forms image of the object from the blue light, the green light, or the red light on the imaging plane of CCD 33 or in its vicinity, respectively. These images are converted into the image signals by CCD 33, respectively. More specifically, the images of the object formed from the blue light, the green light or the red light, respectively, are converted into the B image signal, the G image signal, and the R image signal, respectively. On the other hand, when the excitation light is emitted from this light guide 34 upon the object, this object emits autofluorescence (light in green region of visible spectrum). Therefore, both the autofluorescence emitted from this object and the excitation light reflected by the object surface enter the objective lens 31. Then, the excitation light cut-off filter 32 blocks wavelength components in the region of the excitation light of a convergent beam emitted from this objective lens, while transmitting the autofluorescence. The autofluorescence that has passed through this excitation light cut-off filter 32 forms image of the object on the imaging plane of the CCD 33 or in its vicinity. This CCD 33 converts the image of the object formed from the autofluorescence into an image signal (F image signal).

Further, the external unit 40 includes a processor consisting of the control part 51 and an image processing part 52 which are connected with each other. The control part 51 is connected to the shutter drive mechanisms 45m, 47m, the sliding mechanism 53 and the motor 54m, respectively. The control part 51 adjusts the beam diameter of the excitation light with the adjustment optical system 50 to make the area of the object illuminated with the visible light and that irradiated with the excitation light coincide by controlling the sliding mechanism 53, switches between the visible light and the excitation light to enter the wheel 54 by controlling the shutter drive mechanisms 45m, 47m, and rotates the wheel 54 at a constant speed in synchronization with both shutters 45, 47 by controlling the motor 54m.

Figure 12:
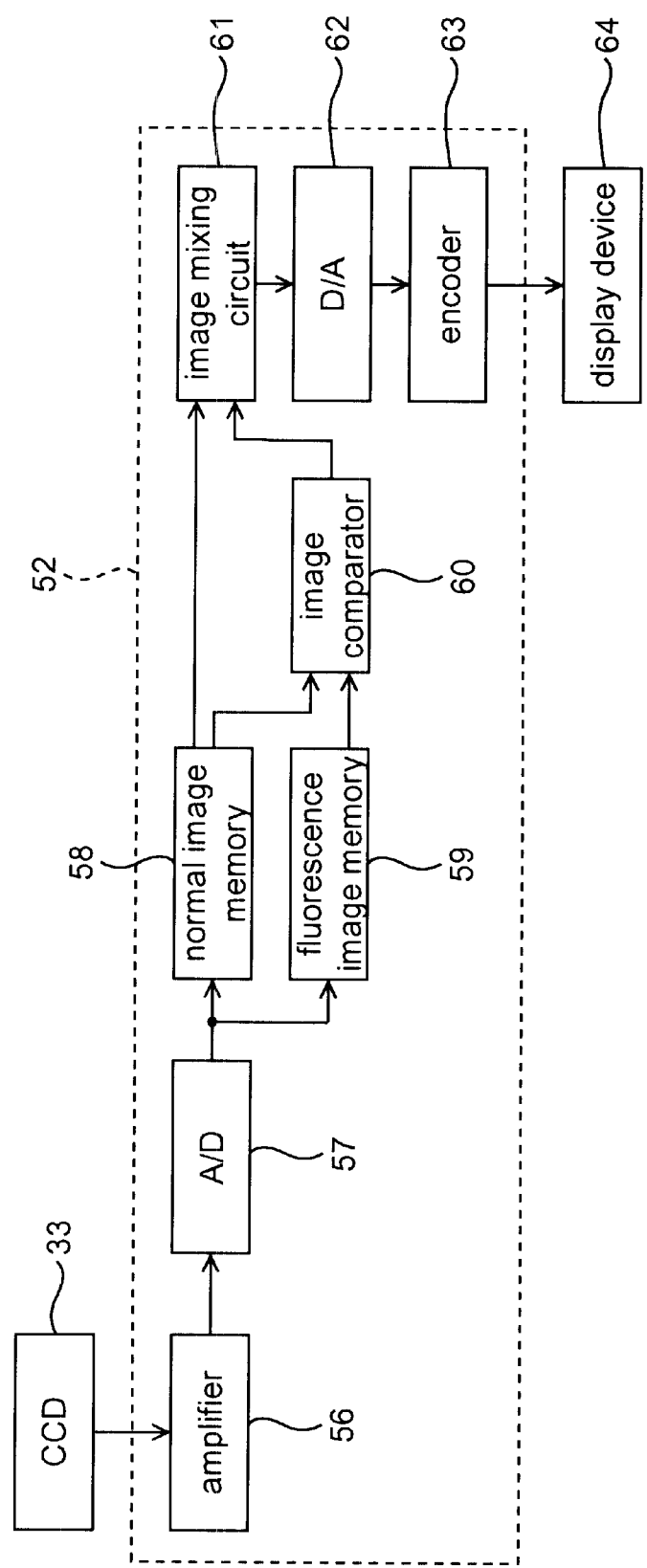
FIG. 12 is a block diagram showing a configuration of the processor.

The image processing part 52 is connected to the CCD 33 and processes the image signal received from this CCD 33. FIG. 12 is a block diagram showing the configuration of the image processing part 52. As shown in FIG. 12, the image processing part 52 has an amplifier 56, an A/D converter 57, normal image memory 58, and fluorescence image memory 59. The amplifier 56 amplifies the B image signal, the G image signal, and the R image signal sent from the CCD 33 at a predetermined normal amplification factor. The amplified signals are analog-to-digital converted by the A/D converter 57 and stored into the normal image memory 58 as synthesized normal image data which is a color image data consisting of a predetermined number of pixels. On the other hand, the amplifier 56 amplifies the F image signal sent from the CCD 33 at a prescribed fluorescence amplification factor. The amplified signal is analog-to-digital converted by the A/D converter 57 and stored in the fluorescence image memory 59 as the fluorescence image data. Note that since the F image signal is weaker than other image signals, this fluorescence amplification factor is set to be larger than the normal amplification factor. This fluorescence image data is stored into the fluorescence image memory 59 as monochromatic image data consisting of a predetermined number of pixels.

The image processing part 52 further has an image comparator 60, an image mixing circuit 61, a D/A converter 62 and an encoder 63. The image comparator 60 is connected to the normal image memory 58 and the fluorescence image memory 59, respectively. The image comparator 60 extracts, from the normal image data in the normal image memory 58, a part corresponding to the R image signal as reference image data. This reference image data is monochromatic image data consisting of a predetermined number of pixels. Further, the image comparator 60 reads the fluorescence image data from the fluorescence image memory 59 and generates specific image data by subtracting the reference image data from this fluorescence image data. This specific image data includes only information corresponding to portions that are potentially abnormal (i.e., portions with weak autofluorescence) in the object. The image mixing circuit 61 is connected to the normal image memory 58 and the image comparator 60, respectively. Further, the image mixing circuit 61 reads the normal image data from the normal image memory 58 and receives the specific image data generated in the image comparator 60. Then, the image mixing circuit 61 generates diagnostic image data by superimposing the specific image data that was colored in a predetermined color (e.g., blue) on the normal image data and outputs it. The D/A converter 62 is connected to the image mixing circuit 61. The D/A converter 62 outputs diagnostic image signal by digital-to-analog converting the diagnostic image data received from the image mixing circuit 61. The encoder 63 is connected to this D/A converter 62 and also connected to a display device 64 that is a television monitor, a personal computer, or the like. The encoder 63 receives a diagnostic image signal output from the D/A converter 62, adds signals (synchronization signal etc.) for displaying image on a screen of the display device 64, and outputs it. The display device 64 displays the diagnostic image as a moving picture in accordance with the signals received from the encoder 63. Note that normal image based on the normal image data may be displayed as a moving picture with the diagnostic image side by side on the same screen.

Figure 13:
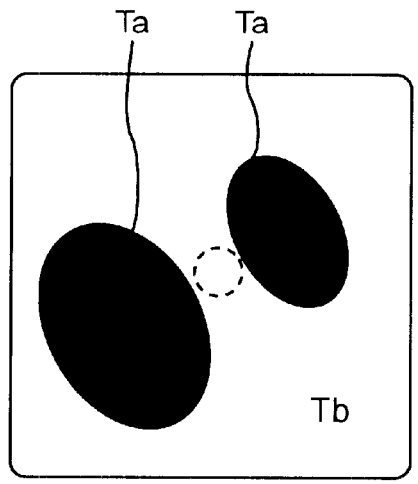
FIG. 13 is a schematic illustration of a normal image and a reference image.
Figure 14:
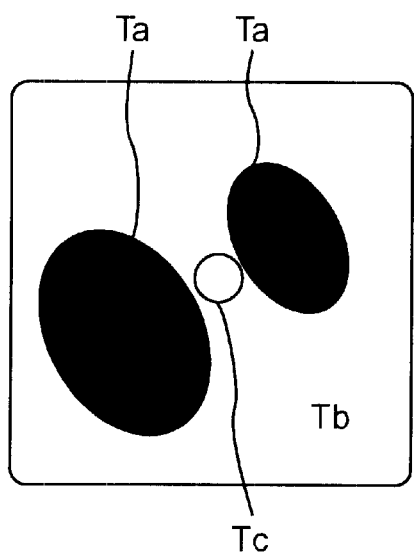
FIG. 14 is a schematic illustration of a fluorescence image.
Figure 15:
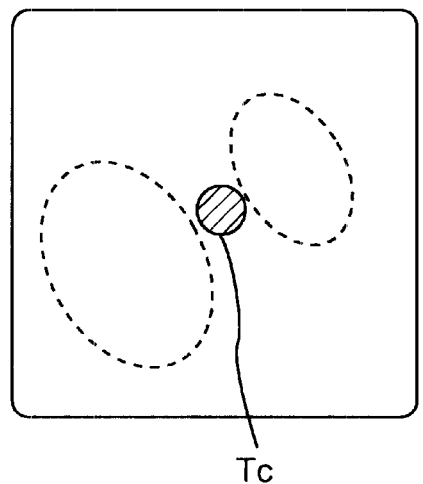
FIG. 15 is a schematic illustration of a specific image.
Figure 16:
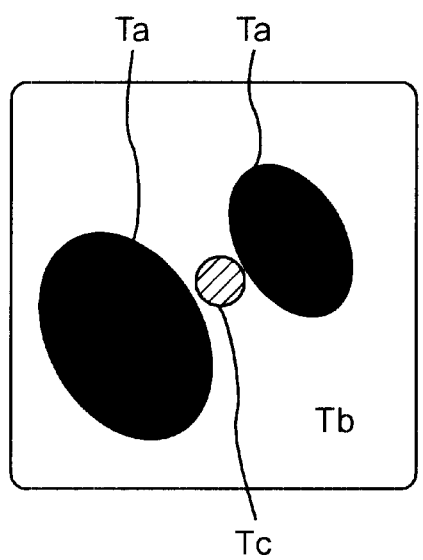
FIG. 16 is a schematic illustration of a diagnostic image.

FIG. 13 is a schematic illustration of the normal image to be displayed based on the normal image data stored in the normal image memory 58. FIG. 14 is a schematic illustration of the fluorescence image to be displayed based on the fluorescence image data stored in the fluorescence image memory 59. In the normal image and the fluorescence image, lumen Ta is indicated in a very dark color because of no substance that reflects light nor emits fluorescence, whereas the tube wall Tb is indicated in a bright color. In addition, diseased tissue Tc of tube wall Tb where the autofluorescence is weak is indicated in the fluorescence image of FIG. 14. Note that the reference image data extracted from the normal image data consists of the R image signal components in the normal image data. Therefore, FIG. 13 also shows a schematic illustration of the reference image to be displayed based on the reference image data. However, actually the normal image data is color image data whereas the reference image data is monochromatic image data. FIG. 15 is a schematic illustration of a specific image to be displayed based on the specific image data output from the image comparator 60. The specific image shown in FIG. 15 is obtained by subtracting the reference image shown in FIG. 13 from the fluorescence image shown in FIG. 14. As shown in FIG. 15, this specific image includes only the diseased tissue Tc, but does not include healthy portions of the tube wall Tb and the lumen Ta. FIG. 16 is a schematic illustration of the diagnostic image that is displayed based on the diagnostic image data output from the image mixing circuit 61. The diagnostic image shown in FIG. 16 is obtained by superimposing the specific image shown in FIG. 15 on the normal image shown in FIG. 13. In this diagnostic image, the diseased tissue Tc is colored in a specific color, for example, blue. Therefore, the operator can correctly recognize a position and a shape of the diseased tissue Tc by observing the diagnostic image displayed on a screen of the display device 64.

As described above, in the video endoscope system of this embodiment, the diameter of the beam emitted from the white light source 41 and the diameter of the beam emitted from the excitation light source 42 are set so that the divergence angle of the red light and the divergence angle of the excitation light, both emitted from the light guide 34, coincide with each other when the second lens 48 is placed at the reference position. Moreover, even if the divergence angle of the red light and the divergence angle of the excitation light, both emitted from light guide 34, differ from each other in case the second lens 48 is placed at the reference position due to geometrical errors, change of the video endoscope or other source, the divergence angle of the red light emitted from light guide 34 and the divergence angle of the excitation angle can be made to coincide by changing the position of second lens 48 to adjust the diameter of the beam emitted from the excitation light source 42. With this adjustment, the area of the object illuminated with the red light and the area irradiated with the excitation light correspond to each other. Under such irradiation conditions, the reference image based on the R image signal and the fluorescence image based on the F image signal represent same area of the object. Therefore the specific image data does not include noises caused by the difference between the illuminated area and the irradiated area, and hence a correct diagnostic image can be obtained.

Figure 17:
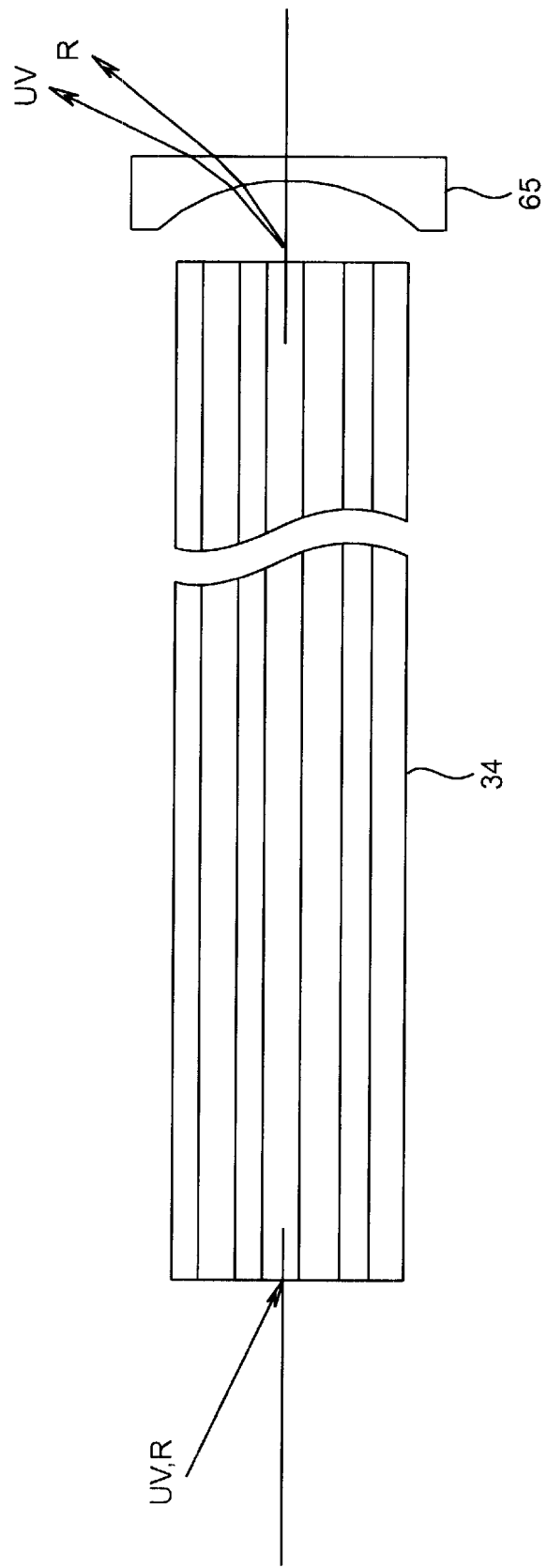
FIG. 17 is an optical configuration diagram showing a variant example that uses a light distribution lens.

In the second embodiment, a light distribution lens 65 as shown in FIG. 17 may be used instead of the cover glass 35. This light distribution lens 65 is a negative lens installed at the distal end of the insertion portion of the video endoscope 1. The distal end face of the light guide 34 faces this light distribution lens 65. A divergent beam emitted from the distal end face of this light guide 34 is further diverged through the light distribution lens 65 and irradiates the object. Assuming that the maximum incident angle of the excitation light (UV) and the maximum incidence angle of the red light (R) with respect to the proximal end face of this light guide 34 correspond with each other, the divergence angle of the excitation light (UV) emitted from the distal end face of the light guide 34 becomes larger than the divergence angle of the red light (R). In addition, if the light distribution lens 65 is composed of a single negative lens, there occurs the difference of the divergence angles due to the chromatic aberration of magnification thereof. More specifically, since the excitation light (UV) has a shorter wavelength than the red light (R), the excitation light is diverged by the light distribution lens 65 with a stronger power than that for red light. Therefore, its designer has to set the beam diameter of the excitation light incident on the condenser lens 55 so as to be smaller than that of the configuration shown in FIG. 11 described above. With such a setting, the maximum incidence angle of the excitation light with respect to the proximal end face of the light guide 34 is further narrowed, and therefore the area irradiated with the excitation light emitted through the light distribution lens 65 and the area illuminated with the red light correspond with each other.

Figure 18:
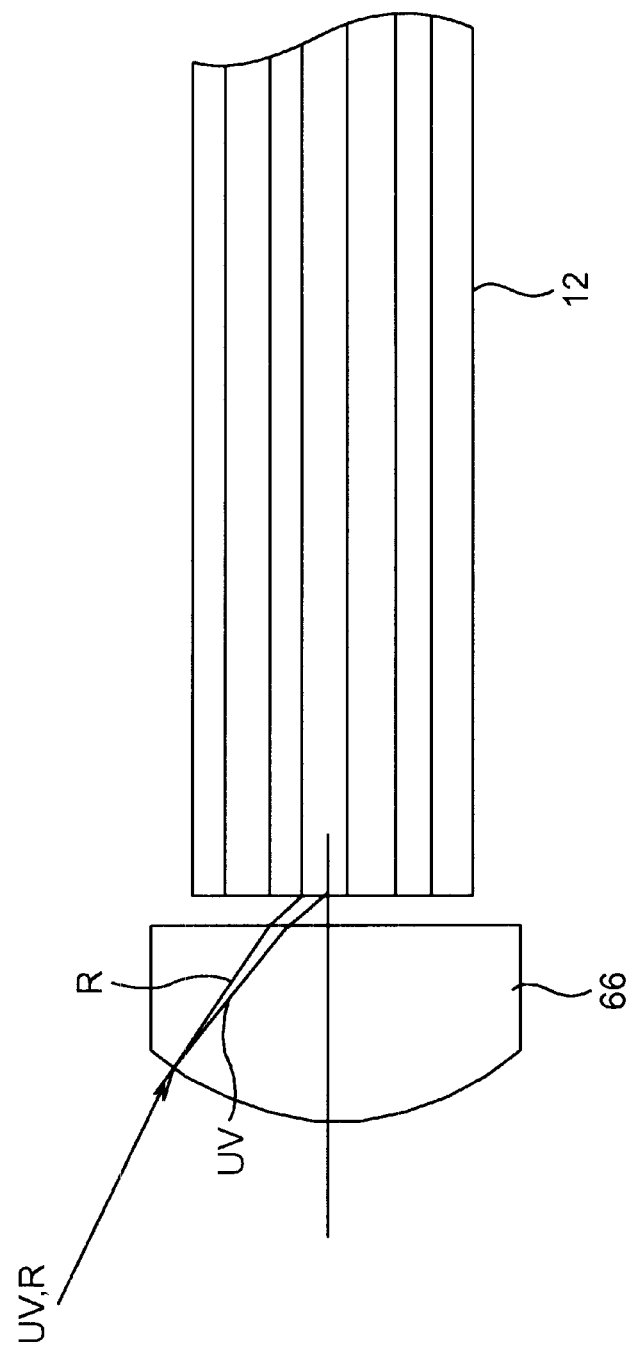
FIG. 18 is an optical configuration diagram showing a variant example that uses a second condenser lens.

In the second embodiment, a second condenser lens 66 may be installed at the proximal end of the light guide flexible tube, not shown in the figure, of video endoscope 30. In the case in which this second condenser lens 66 is a single positive lens, as shown in FIG. 18, the chromatic aberration of magnification for this second condenser lens 66 needs to be considered. Since the excitation light has a shorter wavelength than the red light, the excitation light is converged by the second condenser lens 66 with a stronger power than that for the red light. For example, assuming that the excitation light and the red light enter the second condenser lens 66 at the same incidence angle, the incidence angle of the excitation light with respect to the proximal end face of the light guide 34 becomes larger than the incidence angle of the red light. Therefore, the designer needs to adjust the beam diameter of the excitation light incident on the condenser lens 55 so as to be further smaller than that of the red light by controlling the motion mechanism 53 with the control part 51. With such an adjustment, the area irradiated with the excitation light emitted through the light distribution lens 65 and the area illuminated with the red light correspond with each other.

In addition, in the second embodiment, the second lens 48 of the adjustment optical system 50 may be a negative lens group consisting of multiple lenses. If the adjustment optical system 50 is thus composed and the motion mechanism 53 is composed so that the whole negative lens group is movable to first lens 49 while relative spacings between multiple lenses in the negative lens group vary in synchronism with the movement of the whole, the beam emitted through the adjustment optical system 50 can be adjusted so that its diameter varies as it is a collimated light beam.

Third Embodiment

Figure 19:
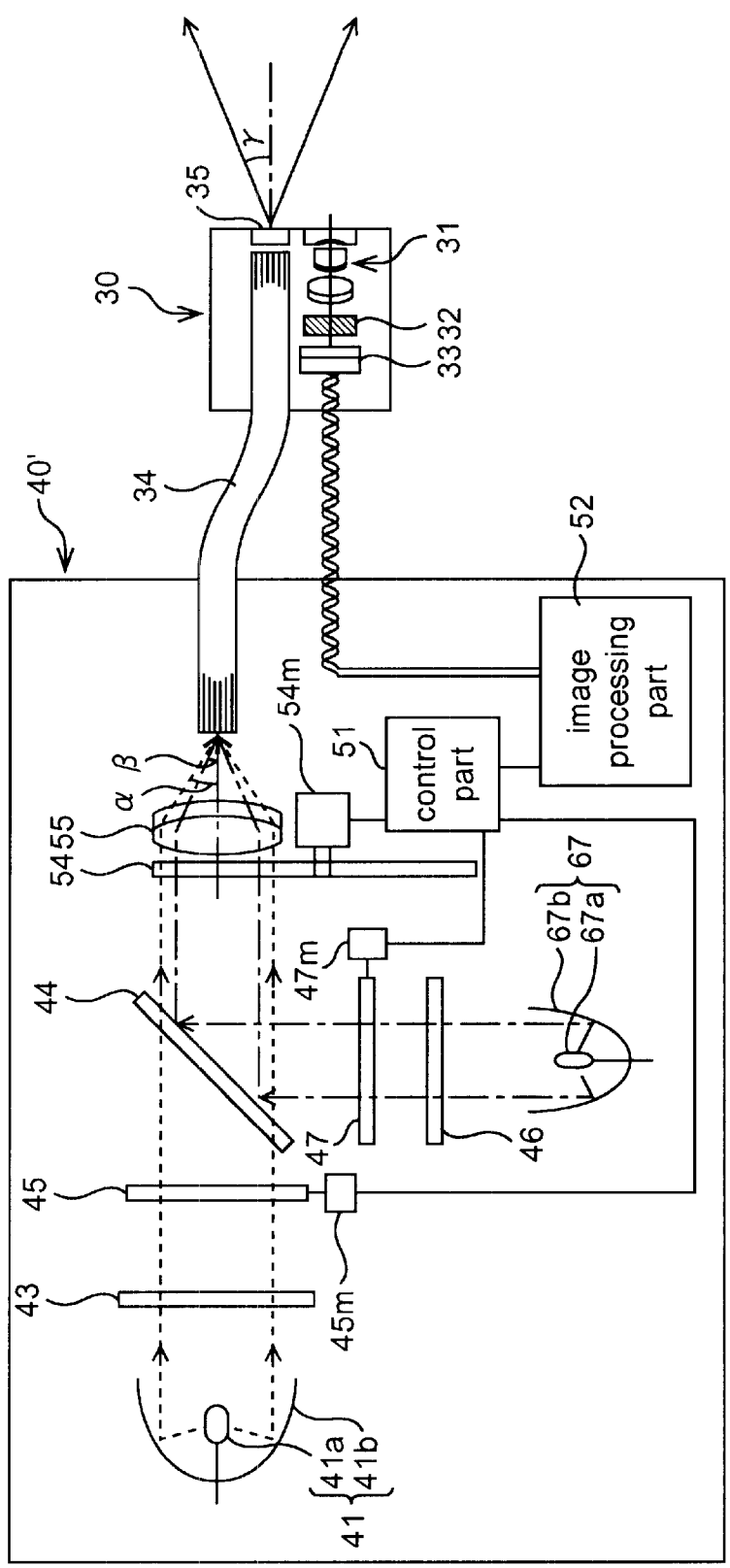
FIG. 19 is a block diagram of the video endoscope system according to the third embodiment of the present invention.

FIG. 19 is an outline block diagram of the video endoscope system according to the third embodiment. The video endoscope system according to the third embodiment, as compared with the video endoscope system according to the above-mentioned second embodiment, differs only in that the size of the an excitation light source 67 is different from that of the excitation light source 42 and that the adjustment optical system 50 is omitted, while other components are common to those of the second embodiment. The excitation light source 67 has a UV lamp 67a for generating light including the ultraviolet light and a reflector 67b. An internal surface of this reflector 67b is formed as a paraboloid of revolution whose diameter is smaller than that of the reflector 41b of the white light source 41. Further, the UV lamp 67a is disposed at a focal position of the paraboloid of revolution inside this reflector 67b. The light generated by the UV lamp 67a is emitted from the excitation light source 67 as a collimated light beam through the reflection by the reflector 67b. Therefore, the diameter of the collimated light beam emitted from the excitation light source 31 is ab into smaller than the diameter of the collimated light beam emitted from the white light source 41. The excitation light filter 46 transmits only wavelength components of the excitation light contained in the collimated light beam emitted from this excitation light source 67. The excitation light emitted from this excitation light filter 46 is reflected by the dichroic mirror 44 and then travels to the wheel 54 whenever having passed through the second shutter 47. The excitation light passes through a transparent component of the wheel 54 and then travels to the condenser lens 55. The beam diameter of the excitation light incident on this condenser lens 55 is smaller than that of the visible light (red light, green light, and blue light). Therefore, the maximum incidence angle $\beta$ of the excitation light with respect to the light guide 34 becomes smaller than the maximum incidence angles $\alpha$ of the red light. Note that the maximum incidence angles $\alpha$ and $\beta$ are the same as those of the above-mentioned first embodiment in the case where the second lens 26 of the adjustment optical system 29 is placed at the standard position, respectively. Therefore, the divergence angle $\gamma$ of the red light emitted from the light guide 34 corresponds to the divergence angle $\gamma$ of the excitation light emitted from the light guide 34.

Fourth Embodiment

Figure 20:
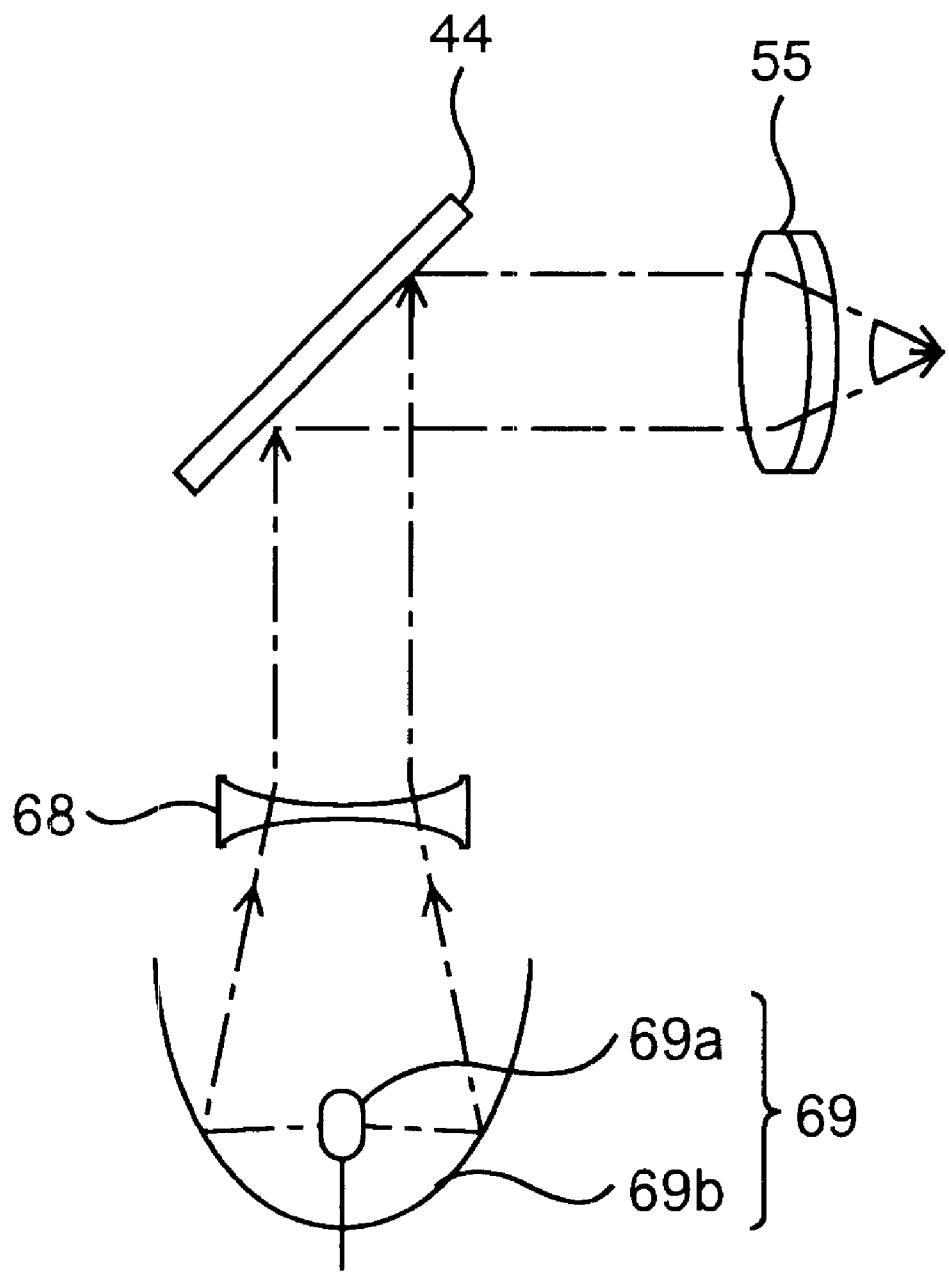
FIG. 20 is a block diagram of the video endoscope system according to a fourth embodiment of the present invention.

The video endoscope system according to the fourth embodiment, as compared with the video endoscope system according to the above-mentioned second embodiment, differs only in that the video endoscope system has an excitation light source 69 for emitting a convergent beam and a beam adjustment lens 68 serving as the adjustment optical system in place of the excitation light source 67 for emitting a collimated beam and the adjustment optical system 50, and other components thereof are common to those of the video endoscope system according to the second embodiment. FIG. 20 illustrates the excitation light source 69 and the beam adjustment lens 68. The excitation light source 69 has a UV lamp 69a for generating light including the ultraviolet light and a reflector 69b. This reflector 69b is a concave mirror, whose internal surface (reflective surface) is formed as an ellipsoid of revolution (more correctly, a surface equivalent to an ellipsoid of revolution divided by a plane that bisects its axis of revolution). The UV lamp 69a is disposed at a focal position of the ellipsoid of revolution inside this reflector 69b (a focal position closer to the reflector 69b). The beam adjustment lens 68 is a negative lens (that is, a divergent optical system), which is arranged so that its rear focus coincides with the other focal position of the ellipsoid of revolution inside the reflector 69b. A divergent beam generated by the UV lamp 69a is emitted from the excitation light source 69 as a convergent beam through reflection by the reflector 69b in the direction of the other focal point. This convergent beam is converted into a collimated light beam through the beam adjustment lens 68. Note that the diameter of the collimated light beam emitted from the beam adjustment lens 68 corresponds to the diameter of the collimated light beam emitted from the adjustment optical system 50 in the second embodiment in case the second lens 48 is placed at the standard position.

Fifth Embodiment

Figure 21:
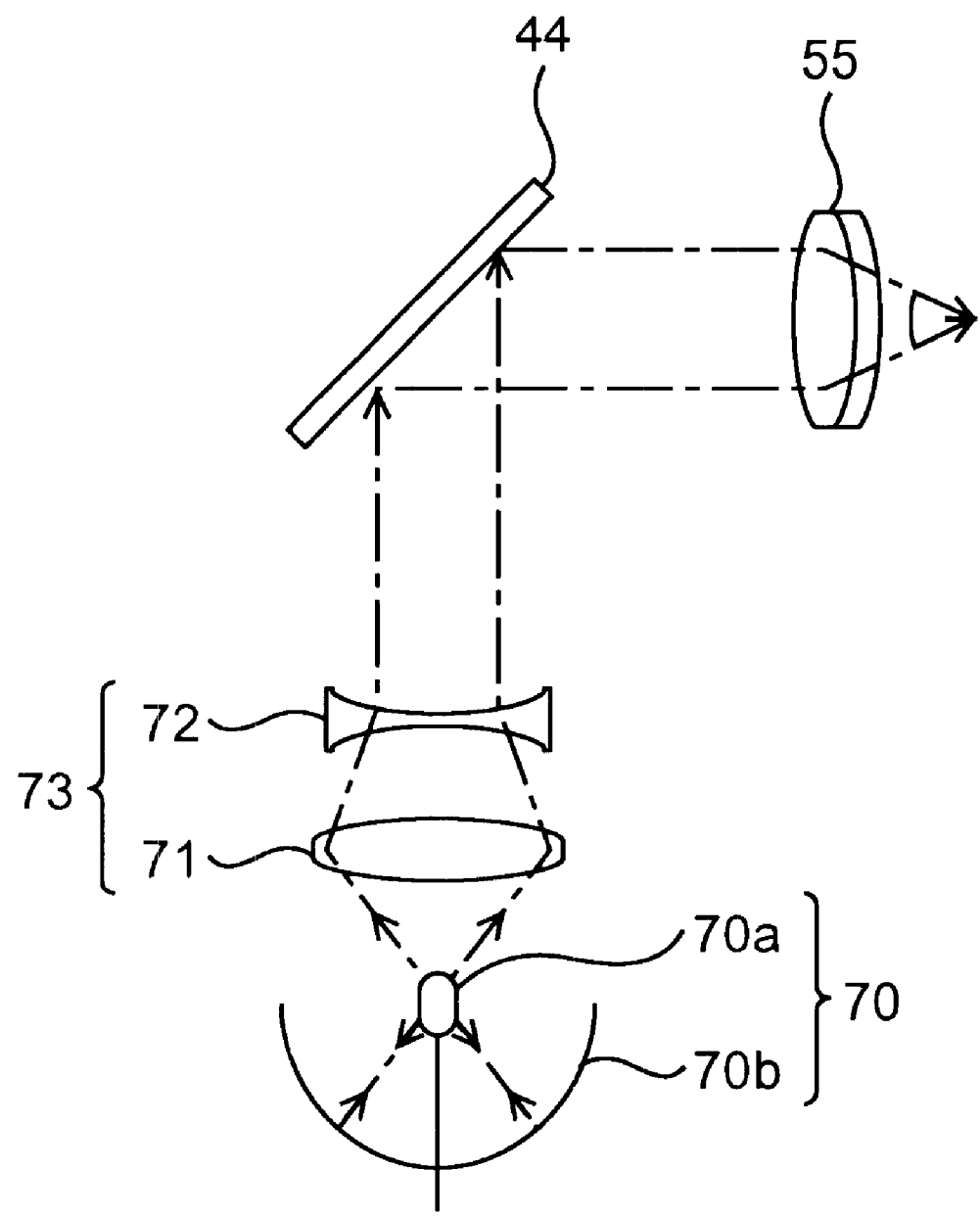
FIG. 21 is an optical configuration diagram of the illumination optical system in the video endoscope system according to a fifth embodiment of the present invention.

The video endoscope system according to the fifth embodiment, as compared with the video endoscope system according to the above-mentioned second embodiment, differs only in that the video endoscope system has an excitation light source 70 for emitting a divergent beam and an adjustment optical system 73 in place of the excitation light source 67 for emitting a collimated beam and the adjustment optical system 50, and other components thereof are common to those of the video endoscope system according to the second embodiment. FIG. 21 illustrates the excitation light source 70 and the adjustment optical system 73. The excitation light source 70 has a UV lamp 70a for generating light including ultraviolet light and a reflector 70b. This reflector 70b is a concave mirror whose internal surface (reflective surface) is formed as a spherical plane. The UV lamp 70a is disposed at the center of the spherical surface of this reflector 70b. The adjustment optical system 73 is composed of a first lens 71 which is a positive lens and a second lens 72 which is a negative lens. These lenses, the first lens 71 and the second lens 72 are arranged so that these optical axes coincide with the center of the reflector 70b. The first lens 71 is arranged at front of the second lens 72. Further, the adjustment optical system 73 is a convergent optical system having a positive refracting power as a whole. The divergent beam generated by the UV lamp 70a is reflected by the reflector 70b toward the UV lamp 70a. The reflected beam that has passed through the UV lamp 70a and then travels as divergent beam is converted into a convergent beam through the first lens 71 and then enters the second lens 72. This second lens 72 converts the convergent beam into a collimated light beam. Note that the diameter of the collimated light beam emitted from the second lens 72 corresponds to the diameter of the collimated light beam emitted from the adjustment optical system 50 in the second embodiment in case the second lens 48 is placed at the standard position.

Sixth Embodiment

Figure 22:
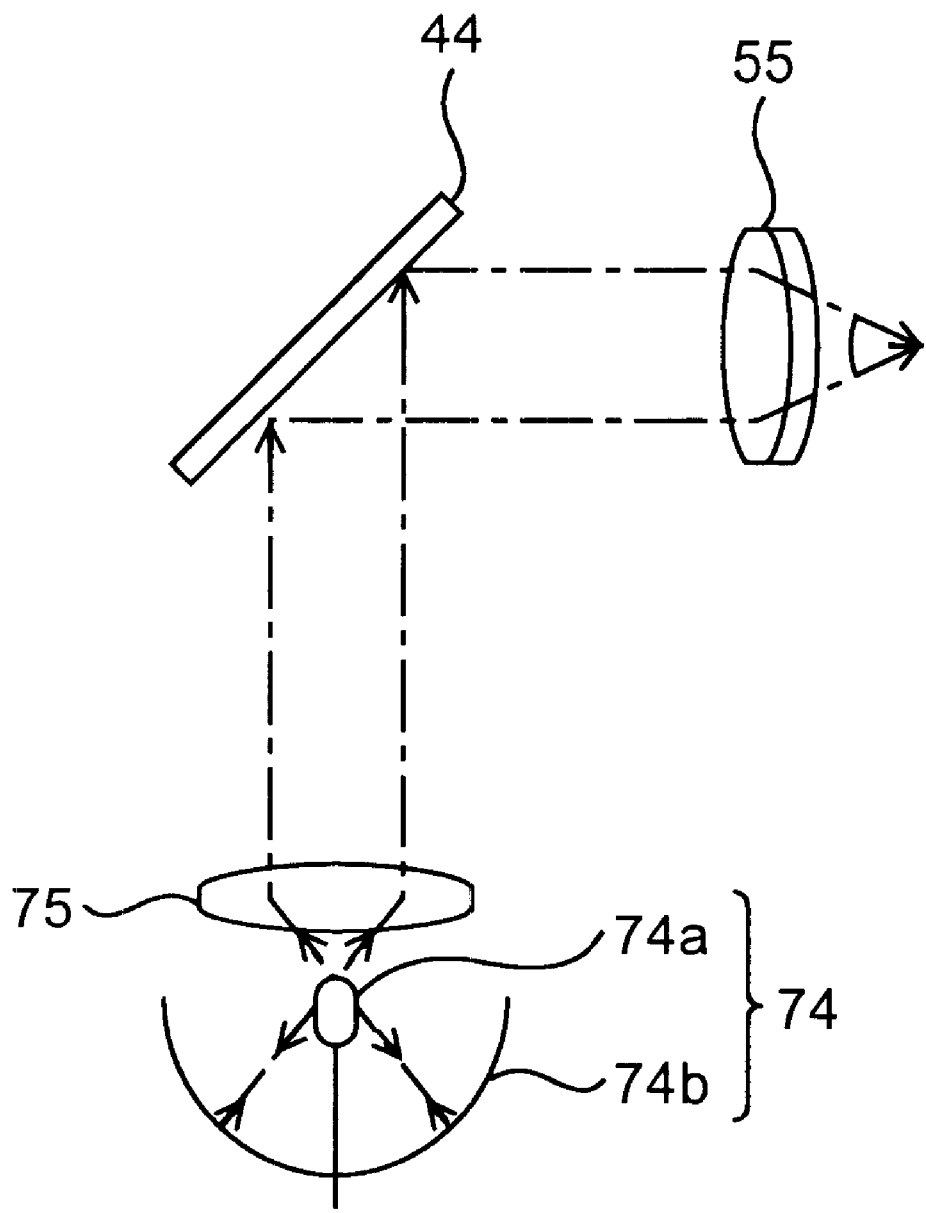
FIG. 22 is an optical configuration diagram of the illumination optical system in the video endoscope system according to a sixth embodiment of the present invention.
Figure 23:
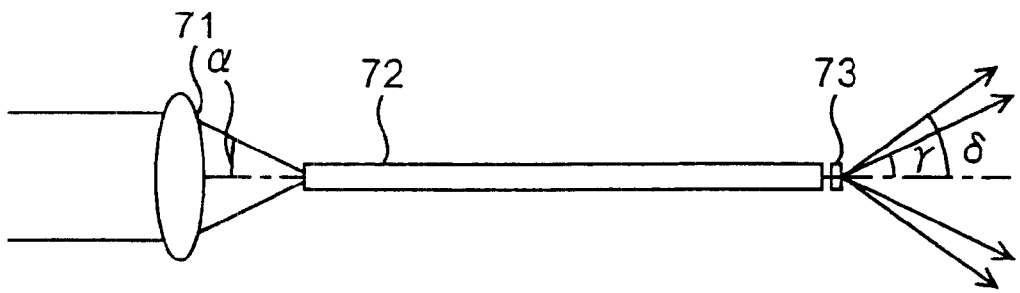
FIG. 23 is an explanatory drawing showing conventional irradiation areas by visible light and by excitation light.

The video endoscope system according to the sixth embodiment, as compared with the video endoscope system according to the above-mentioned second embodiment, differs only in that the video endoscope system has an excitation light source 74 for emitting a divergent beam and a beam adjustment lens 75 serving as a adjustment optical system in place of the excitation light source 67 for emitting a collimated beam and the adjustment optical system 50, and other components thereof are common to those of the video endoscope system according to the second embodiment. FIG. 22 illustrates the excitation light source 74 and the beam adjustment lens 75. The excitation light source 74 has a UV lamp 74a for generating light including the ultraviolet light and a reflector 74b. This reflector 74b is a concave mirror whose internal surface (reflective surface) is formed as a spherical plane. The UV lamp 74a is disposed at the center of the spherical surface of the reflector 74b. The beam adjustment lens 75 is a positive lens (convergent optical system) and is arranged so that the front focal point coincides with a position of the UV lamp 74a. Then, a divergent beam generated by the UV lamp 74a is reflected by the reflector 74b toward the UV lamp 74a. The reflected beam that has passed the UV lamp 74a then travels as divergent beam is converted into a collimated light beam through the beam adjustment lens 75. Note that the diameter of the collimated light beam emitted from the beam adjustment lens 75 corresponds to the diameter of the collimated light beam emitted from the adjustment optical system 50 in the second embodiment in case the second lens 48 is placed at the standard position.

The video endoscope system according to the present invention composed as described above can make the area of the object irradiated with the excitation light and the area illuminated with the visible light correspond to each other. Therefore, the fluorescence image signal and the reference image signal are acquired under such a condition that the both areas of the object correspond to each other. Therefore, the diagnostic image that indicates the state of the object correctly can be obtained based on the fluorescence image signal and the reference image signal.

What is claimed is:

1. An illumination optical system comprising:
    a light guide that has a fiber bundle for emitting a light beam incident upon its proximal end face through its distal end face;
    a visible lamp for generating visible light;
    a first optical system for forming the visible light generated by the visible lamp into a collimated light beam;
    an excitation lamp for generating excitation light that excites living tissue to cause fluorescence;
    a second optical system for forming excitation light generated by the excitation light lamp into a collimated light beam whose diameter is smaller than that of the collimated light beam of the visible light formed by the first optical system;
    a switching mechanism that alternately guides the visible light formed into the collimated light beam by the first optical system and the excitation light formed into the collimated light beam by the second optical system to a common optical path; and
    a condenser optical system that converges the visible light and the excitation light guided by the switching mechanism to the common optical path onto the proximal end face of said fiber bundle.

2. An illumination optical system according to claim 1, wherein said second optical system has a reflector for reflecting the excitation light generated by said excitation light lamp as a collimated light beam and an adjustment optical system for adjusting the beam diameter of the excitation light reflected by this reflector.

3. An illumination optical system according to claim 2, wherein said adjustment optical system is composed of multiple lenses and capable of varying the beam diameter of the excitation light reflected by said reflector through movement of a part of the multiple lenses in the direction of the optical axis.

4. An illumination optical system according to claim 1, wherein said second optical system is composed only of a reflector for reflecting the excitation light generated by said excitation light lamp as a collimated light beam.

5. An illumination optical system according to claim 1, wherein said second optical system has a reflector for reflecting the excitation light generated by said excitation light lamp as a convergent beam and a negative lens system for converting the excitation light reflected by the reflector into a collimated light beam.

6. An illumination optical system according to claim 1, wherein said second optical system has a reflector for reflecting the excitation light generated by said excitation light lamp as a divergent beam and a positive lens system for converting the excitation light reflected by the reflector into a collimated light beam.

7. An illumination optical system comprising:
a light guide that has a fiber bundle for emitting a beam incident upon its proximal end face through its distal end face;
a first light source for emitting a beam in a predetermined first wavelength region;
a second light source for emitting a beam in a second wavelength region which is on a shorter wavelength side than said first wavelength region;
a switching mechanism for alternatively guiding the beams emitted from these light sources toward the proximal end of said light guide;
a condenser lens positioned in the optical path between said light guide and said switching mechanism to converge the beam guided by said switching mechanism onto the proximal end face of the fiber bundle; and
an adjustment optical system that adjusts a maximum incidence angle of the beam in said second wavelength region with respect to the proximal end face of said fiber bundle so as to be smaller than a maximum incidence angle of the beam in said first wavelength region with respect to the proximal end face of said fiber bundle so that the divergence angle of the beam in the first wavelength region emitted from the distal end face of said fiber bundle may be equal to the divergence angle of the beam in the second wavelength region emitted from the distal end face of said fiber bundle.

8. An illumination optical system according to claim 7, wherein said adjustment optical system adjusts diameter of the beam in the second wavelength region incident on said condenser lens so as to be smaller than diameter of the beam in the first wavelength region incident on said condenser lens.

9. An illumination optical system according to claim 7, wherein each of said light sources emits a collimated light beam, respectively, and
said adjustment optical system has a condenser optical system and a divergent optical system each of which is arranged along the optical path between either of said light sources and said switching mechanism to reduce diameter of the collimated light beam in said second wavelength region.

10. An illumination optical system according to claim 7, wherein one of said light sources emits a convergent beam,
the other of said light sources emits a collimated light beam, and
said beam adjustment optical system has a divergent optical system positioned in an optical path between the light source emitting the convergent beam and said switching mechanism, converts the incident convergent beam into a collimated light beam having a diameter different from that of the collimated light beam emitted from the other of said light sources.

11. An illumination optical system according to claim 7, wherein one of said light sources emits a divergent beam, the other of said light sources emits a collimated light beam,
said beam adjustment optical system has a convergent optical system positioned in an optical path between the light source emitting the divergent beam and said switching mechanism, converts the incident convergent beam into a collimated light beam having a diameter different from that of the collimated light beam emitted from the other of said light sources.

12. An illumination optical system according to claim 7, wherein said first light source emits the visible light, and
said second light source part emits excitation light that is the ultraviolet light in a predetermined wavelength region that excites the living tissue to cause autofluorescence.

13. A video endoscope system comprising:
a light-guide optical system that has a fiber bundle for emitting a beam incident on its proximal end face through its distal end face toward an object;
a visible light lamp for generating visible light;
a first optical system for forming the visible light generated by the visible light lamp into a collimated light beam;
an excitation light lamp for generating excitation light that excites living tissue to cause fluorescence;
a second optical system for forming the excitation light generated by the excitation light lamp into a collimated light beam of which diameter is smaller than that of a collimated light beam of the visible light formed by the first optical system;
a switching mechanism that alternately guides the visible light formed into the collimated light beam by the first optical system and the excitation light formed into the collimate light beam by the second optical system to a common optical path;
a condenser lens that converges the visible light and the excitation light alternately guided by the switching mechanism onto the proximal end face of said fiber bundle;
an objective optical system that focuses wavelength components of the light from a surface of the object other than the excitation light to form an image of the object;
an imaging device that picks up an image of the object formed by said objective optical system to convert it into an image signal; and
a processor that forms a reference image signal based on the image signal that is acquired by the imaging device during a period when the visible light is guided by said switching mechanism and forms a fluorescence image signal based on the image signal that is acquired by the imaging device during a period when the excitation light was guided by said switching mechanism.

14. A video endoscope system comprising:
a light-guide optical system that has a fiber bundle for emitting a beam incident on its proximal end face through its distal end face toward an object;
a light source unit that emits the visible light and the excitation light that excites living tissue to cause fluorescence, alternately guides the visible light and the excitation light to common optical path, and converges the guided light onto the proximal end face of said fiber bundle;
an adjustment optical system that adjusts a maximum incidence angle of the excitation light with respect to the proximal end face of said fiber bundle so as to be smaller than the maximum incidence light of the visible light with respect thereto;

an objective optical system that converges wavelength components of light from the surface of the object other than the excitation light to form an image of the object;

an imaging device that picks up an image of an object formed by said objective optical system to convert it into an image signal;

a processor that forms a reference image signal based on the image signal that is acquired by the imaging device during a period when the visible light is guided by said light source unit and forms a fluorescence image signal based on the image signal that is acquired by the imaging device during a period when the excitation light is guided by said light source unit.

15. A video endoscope system according to claim 14, wherein said processor compares said reference image signal and said fluorescence image signal obtained when a chart which reflects the visible light and emits fluorescence with irradiation of the excitation light is alternatively illuminated with the visible light and irradiated with the excitation light, and controls said adjustment optical system so that the area illuminated with the visible light and the area irradiated with the excitation light may correspond to each other on the basis of result of the comparison, whereby said processor relatively varies the maximum incident angle of the visible light and the maximum incident angle of the excitation light with respect to the proximal end face of said fiber bundle.

16. A video endoscope system according to claim 15, wherein said processor amplifies at least one of said fluorescence image signal and said reference image signal so that both image signals become the same level as each other, digitizes a differential signal between said fluorescence image signal and said reference image signal after the amplification with reference to a predetermined threshold, and then judges that the area of the chart irradiated with the excitation light and the area of the chart illuminated with the visible light correspond to each other in case the digitized differential signal is zero in the whole irradiation area.

17. A video endoscope system according to claim 14, wherein said adjustment optical system makes the divergence angle of the excitation light emitted through a distal end face of said fiber bundle correspond to the divergence angle of the visible light emitted through the distal end face of said fiber bundle by adjusting the maximum incidence angle of the excitation light with respect to the proximal end face of said fiber bundle so as to be smaller than the maximum incidence angle of the visible light with respect to the proximal end face of said fiber bundle.

18. A video endoscope system according to claim 14, wherein said light source unit has:
   a visible light source for generating the visible light;
   an excitation light source for generating the excitation light;
   a switching mechanism that alternately guides the visible light and the excitation light to the proximal end face of said fiber bundle; and
   a condenser lens that is positioned in the optical path between said fiber bundle and said switching mechanism to converge the beam guided by said switching mechanism onto the proximal end face of said fiber bundle,
   and wherein said adjustment optical system varies the beam diameter of at least one of the visible light and the excitation light incident on said condenser lens.

19. A video endoscope system according to claim 18, wherein said adjustment optical system includes at least one lens and a motion mechanism for displacing the lens in the direction of its optical axis, and said processor varies the diameter of the beam emitted from said adjustment optical system by controlling said motion mechanism.

20. A video endoscope system according to claim 18, wherein said switching mechanism has:
   a first light blocking member for blocking said visible light by being inserted in the optical path of the visible light emitted from said visible light source;
   a second blocking member for blocking said excitation light by being inserted in the optical path of the excitation light emitted from said excitation light source; and
   a switching drive mechanism that blocks the excitation light with said second blocking member while retracting said first blocking member from the visible light and blocks the visible light with said first blocking member while retracting said second blocking member from the excitation light.

21. A video endoscope system according to claim 20, wherein said first light blocking member is a first rotary shutter having a visible light transmission part for allowing the visible light to pass therethrough which is formed in a predetermined portion in an area along its circumferential,
   said second light blocking member is a second rotary shutter having an excitation light transmission part for allowing the excitation light to pass therethrough which is formed in a predetermined portion in an area along its circumferential, and
   said switching drive mechanism rotates these rotary shutters, respectively, so that the excitation light transmission part of said second rotary shutter is inserted into the optical path of the excitation light while said first rotary shutter blocking the visible light and so that the visible light transmission part of said first rotary shutter is inserted into the optical path of the visible light while said second rotary shutter blocking the excitation light.

22. A video endoscope system according to claim 14, wherein said processor generates a diagnostic image signal by subtracting the fluorescence image signal from the reference image signal.

23. A video endoscope system comprising:
   a light guide that has a fiber bundle for emitting a beam incident upon its a proximal end face through its distal end face toward an object;
   a first light source for emitting visible light;
   a second light source for emitting excitation light that is ultraviolet light in a predetermined wavelength region that excites living tissue to cause autofluorescence;
   a switch mechanism for alternatively guiding the visible light and the ultraviolet light toward the proximal end face of said fiber bundle;
   a condenser lens that is positioned in the optical path between said fiber bundle and said switching mechanism to converge the light guided by said switching mechanism onto the proximal end face of the fiber bundle;
   an adjustment optical system that adjusts a maximum incidence angle of said excitation light with respect to the proximal end face of said fiber bundle so as to be smaller than a maximum incidence angle of said visible light with respect to the proximal end face of said fiber bundle so that a divergence angle of the visible light emitted from the distal end face of said light guide and the divergence angle of the excitation light emitted from the distal end face of said fiber bundle correspond to each other;

an objective optical system for focusing wavelength components of light from a surface of the object, other than the excitation light to form an image of the object;

an imaging device for picking up an image of the object formed by said objective optical system to convert it into an image signal; and a processor that controls the switching mechanism so that said visible light and said excitation light enter said fiber bundle alternately and repeatedly, generates normal image data based on an image signal that is acquired by the imaging device during a period when the visible light is guided by said switching optical system, generates fluorescence image data based on an image signal that is acquired by the imaging device during a period when the excitation light is guided by said switching optical system, obtains reference image data from said normal image data, extracts specific image data by subtracting the obtained reference image data from said fluorescence image data, and generates diagnostic image data to be displayed as a moving picture by superimposing the extracted specific image data on said normal image data.

* * * * *